US012760373B2

(12) United States Patent
Iwai et al.

(10) Patent No.: US 12,760,373 B2
(45) Date of Patent: Oct. 13, 2026

(54) BIOMARKERS FOR PREDICTING THE RESPONSE TO CHECKPOINT INHIBITORS

(71) Applicant: Chugai Seiyaku Kabushiki Kaisha, Tokyo (JP)

(72) Inventors: Toshiki Iwai, Kanagawa (JP); Masamichi Sugimoto, Kanagawa (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 849 days.

(21) Appl. No.: 17/912,257

(22) PCT Filed: Mar. 19, 2021

(86) PCT No.: PCT/JP2021/011302
§ 371 (c)(1),
(2) Date: Sep. 16, 2022

(87) PCT Pub. No.: WO2021/187615
PCT Pub. Date: Sep. 23, 2021

(65) Prior Publication Data

US 2023/0146730 A1 May 11, 2023

(30) Foreign Application Priority Data

Mar. 19, 2020 (JP) ................................ 2020-048845

(51) Int. Cl.
*C12Q 1/6886* (2018.01)
*G01N 33/5752* (2026.01)

(52) U.S. Cl.
CPC ....... *C12Q 1/6886* (2013.01); *G01N 33/5752* (2026.01); *C12Q 2600/106* (2013.01);
(Continued)

(58) Field of Classification Search
CPC ............ C12Q 1/6886; C12Q 2600/106; C12Q 2600/158; G01N 33/57423; G01N 2333/521
See application file for complete search history.

(56) References Cited

U.S. PATENT DOCUMENTS

| | | | |
|---|---|---|---|
| 2015/0071910 | A1 | 3/2015 | Kowanetz et al. |
| 2019/0346444 | A1 | 11/2019 | Klein et al. |

FOREIGN PATENT DOCUMENTS

| | | | |
|---|---|---|---|
| CN | 101711286 A | 5/2010 | |
| WO | WO 2008/122007 A1 | 10/2008 | |

(Continued)

OTHER PUBLICATIONS

Bottcher, J.P. et al. Trends in Cancer 4(11):784. (Nov. 2018) (Year: 2018).*

(Continued)

*Primary Examiner* — Diana B Johannsen
(74) *Attorney, Agent, or Firm* — Fish & Richardson P.C.

(57) ABSTRACT

The invention provides biomarkers for predicting the response to checkpoint inhibitors. The inventors demonstrate that a PD-1/PD-L1 inhibitor exerts antitumor activity against tumor with low PD-L1 expression and immune-desert phenotype through blocking PD-L1 in the lymph nodes. The invention provides novel combinations of intra-tumoral markers for antigen cross-presenting cells and T cell chemokines which are expected to be superior efficacy-predicting biomarkers compared to existing methods.

8 Claims, 13 Drawing Sheets

Specification includes a Sequence Listing.

(52) U.S. Cl.
CPC . *C12Q 2600/158* (2013.01); *G01N 2333/521* (2013.01); *G01N 2333/70517* (2013.01)

(56) References Cited

FOREIGN PATENT DOCUMENTS

| | | | |
|---|---|---|---|
| WO | WO 2015/120382 | | 8/2015 |
| WO | WO 2016/073760 | A1 | 5/2016 |
| WO | WO 2016/168133 | | 10/2016 |
| WO | WO 2017/013436 | | 1/2017 |
| WO | WO 2017/147554 | A2 | 8/2017 |
| WO | WO 2017/176925 | | 10/2017 |
| WO | WO 2017/190074 | A1 | 11/2017 |
| WO | WO 2018/055145 | | 3/2018 |
| WO | WO 2018/191660 | | 10/2018 |
| WO | WO 2018/209324 | | 11/2018 |
| WO | WO 2018/225063 | | 12/2018 |
| WO | WO 2018/231771 | | 12/2018 |
| WO | WO 2020/014460 | A1 | 1/2020 |
| WO | WO 2021/187615 | | 9/2021 |

OTHER PUBLICATIONS

Vilgelm, A.E. et al. Frontiers in Immunology 10:333 (pp. 1-13). (Feb. 2019) (Year: 2019).*
Butte et al., "Programmed Death-1 Ligand 1 Interacts Specifically with the B7-1 Costimulatory Molecule to Inhibit T Cell Responses," Immunity, Jul. 2007, 27(1):111-122.
Butte et al., "Interaction of human PD-L1 and B7-1," Mol Immunol, Aug. 2008, 45(13):3567-3572.
Chow et al., "Intratumoral activity of the CXCR3 chemokine system is required for the efficacy of anti-PD-1 therapy," Immunity, Jun. 18, 2019, 50(6):1498-1512. e5.
Curiel et al., "Blockade of B7-H1 improves myeloid dendritic cell-mediated antitumor immunity," Nat Med, May 2003, 9(5):562-567.
Gottschalk et al., "Batf3-dependent dendritic cells in the renal lymph node induce tolerance against circulating antigens," J Am Soc Nephrol, 2013, 24(4):543-549.
Gros et al., "PD-1 identifies the patient-specific CD8+ tumor-reactive repertoire infiltrating human tumors," J Clin Invest, May 2014, 124(5):2246-2259.
Iwai et al., "Mechanism of action of anti-PD-L1 antibody in a PD-L1-negative and immune desert-like tumor model," Cancer Res, Jul. 2019, 79 (13_Supplement):Abstract 4995.
Iwai et al., "Analysis of Mechanism of Action of Atezolizumab in PD-L1 Negative Tumors and Exploration of New Biomarkers," Haigan (Japanese Journal of Lung Cancer), 2020, 60(6):597 (with English translation).
Iwai et al., "Analysis of Mechanism of Action of Anti-PD-L1 Antibodies against PD-L1 Negative Tumors and Exploration of New Mechanism-Based Predictive Biomarkers of Response," Program and Abstracts of the 24th Annual Meeting of Japanese Association of Cancer Immunology, Sep. 23, 2020, p. 72 (with English translation).
Mayoux et al., "Dendritic cells dictate responses to PD-L1 blockade cancer immunotherapy," Science Translational Medicine, Mar. 11, 2020, 12(534):1-11.
Rittmeyer et al., "Atezolizumab versus docetaxel in patients with previously treated non-small-cell lung cancer (OAK): a phase 3, open-label, multicentre randomized controlled trial," Lancet, Jan. 21, 2017, 389(10066):255-265.
Van De Ven et al., "High PD-1 expression on regulatory and effector T-cells in lung cancer draining lymph nodes," ERJ Open Res, May 23, 2017, 3(2):00110-02016.
Zou et al., "PD-L1 (B7-H1) and PD-1 pathway blockade for cancer therapy: Mechanisms, response biomarkers and combinations," Sci Transl Med, Mar. 2, 2016, 8(328):328rv4.
International Search Report in PCT/JP2021/011302, mailed Jun. 8, 2021, 3 pages.
International Preliminary Report on Patentability in PCT/JP2021/011302, mailed Sep. 20, 2022, 5 pages.
Luo et al., "Cisplatin Facilitates Radiation-Induced Abscopal Effects in Conjunction with PD-1 Checkpoint Blockade Through CXCR3/CXCL10-Mediated T-cell Recruitment," Clin Cancer Res, Dec. 1, 2019, 25(23):7243-7255.
Mikucki et al., "Non-redundant requirement for CXCR3 signaling during tumoricidal T-cell trafficking across tumor vascular checkpoints," Nat Commun, Jun. 25, 2015, 6:7458, 30 pages.
Nagaya et al., "Near infrared photoimmunotherapy with avelumab, an anti-programmed death-ligand 1 (PD-L1) antibody," Oncotarget, Jan. 31, 2017, 8(5):8807-8817.
Inman et al., "Atezolizumab: A PD-L1-Blocking Antibody for Bladder Cancer," Clin Cancer Res, Apr. 15, 2017, 23(8):1886-1890.
Kowanetz et al., "Differential regulation of PD-L 1 expression by immune and tumor cells in NSCLC and the response to treatment with atezolizumab (anti-PD-L1)," Proc Natl Acad Sci USA, Oct. 23, 2018, 115(43):E10119-E10126.
Saleh et al., "PD-L1 Blockade by Atezolizumab Downregulates Signaling Pathways Associated with Tumor Growth, Metastasis, and Hypoxia in Human Triple Negative Breast Cancer," Cancers (Basel), Jul. 25, 2019, 11(8):1050, 17 pages.

* cited by examiner

[Fig. 1]
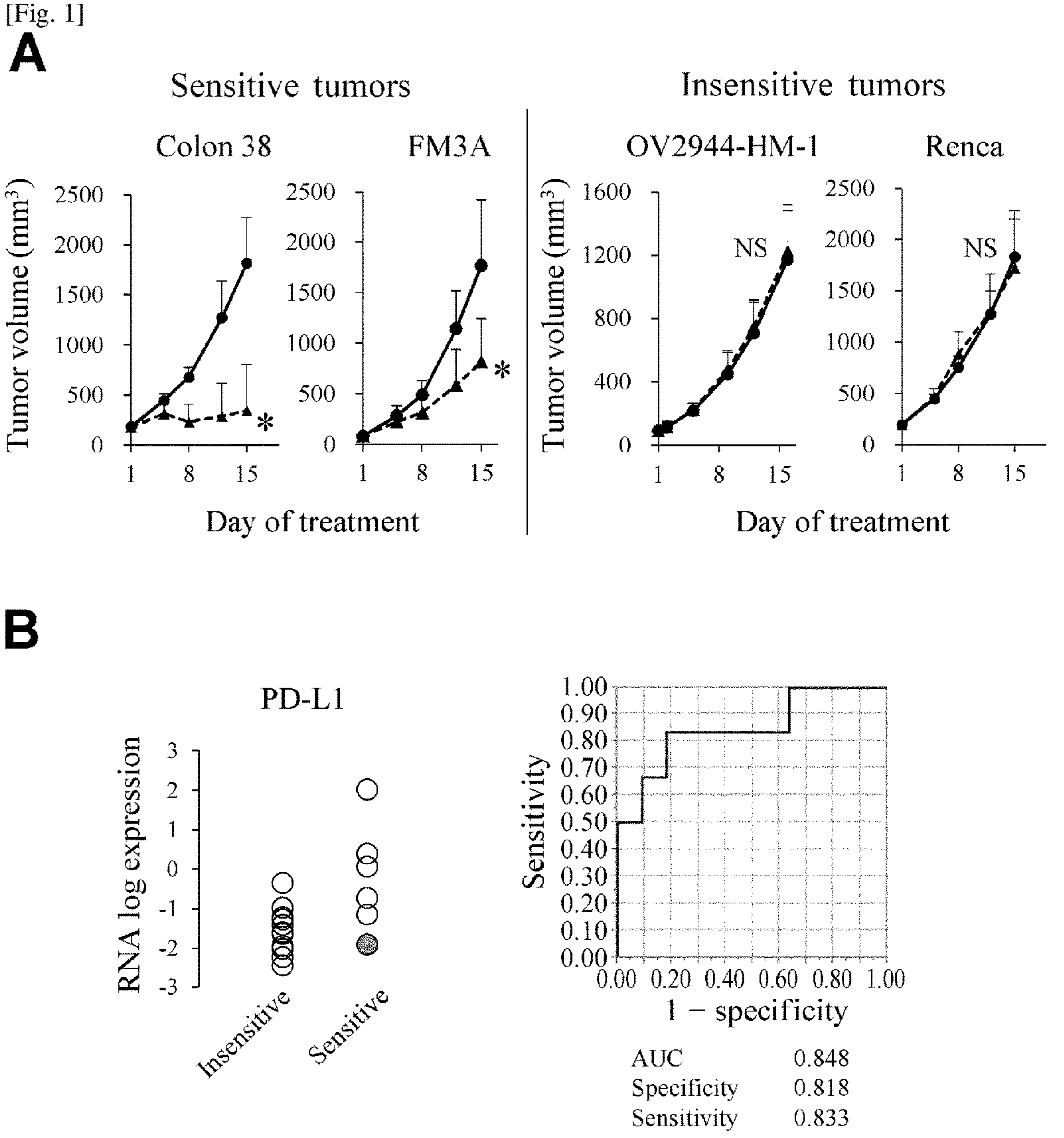

[Fig. 2]
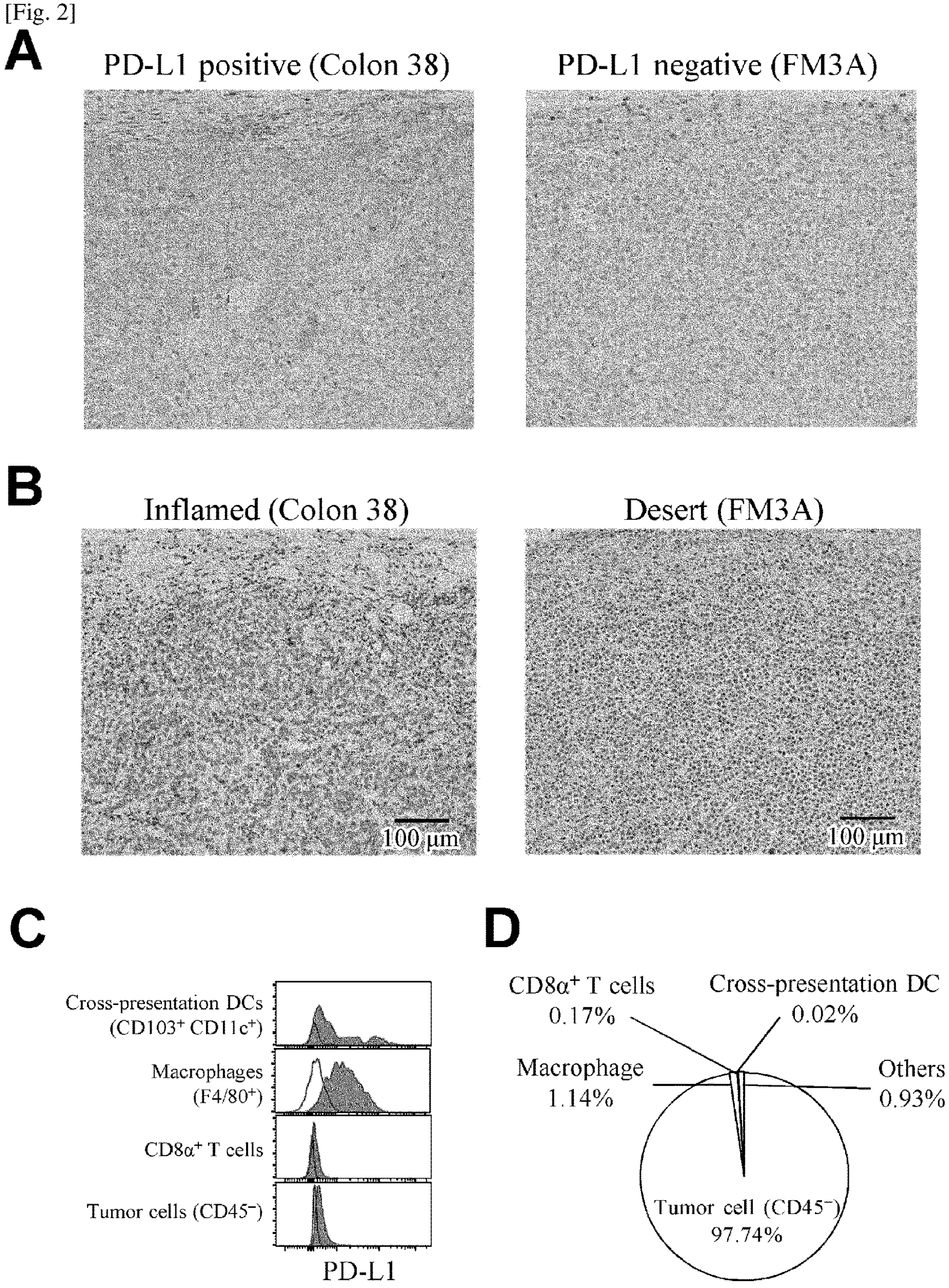

[Fig. 3]
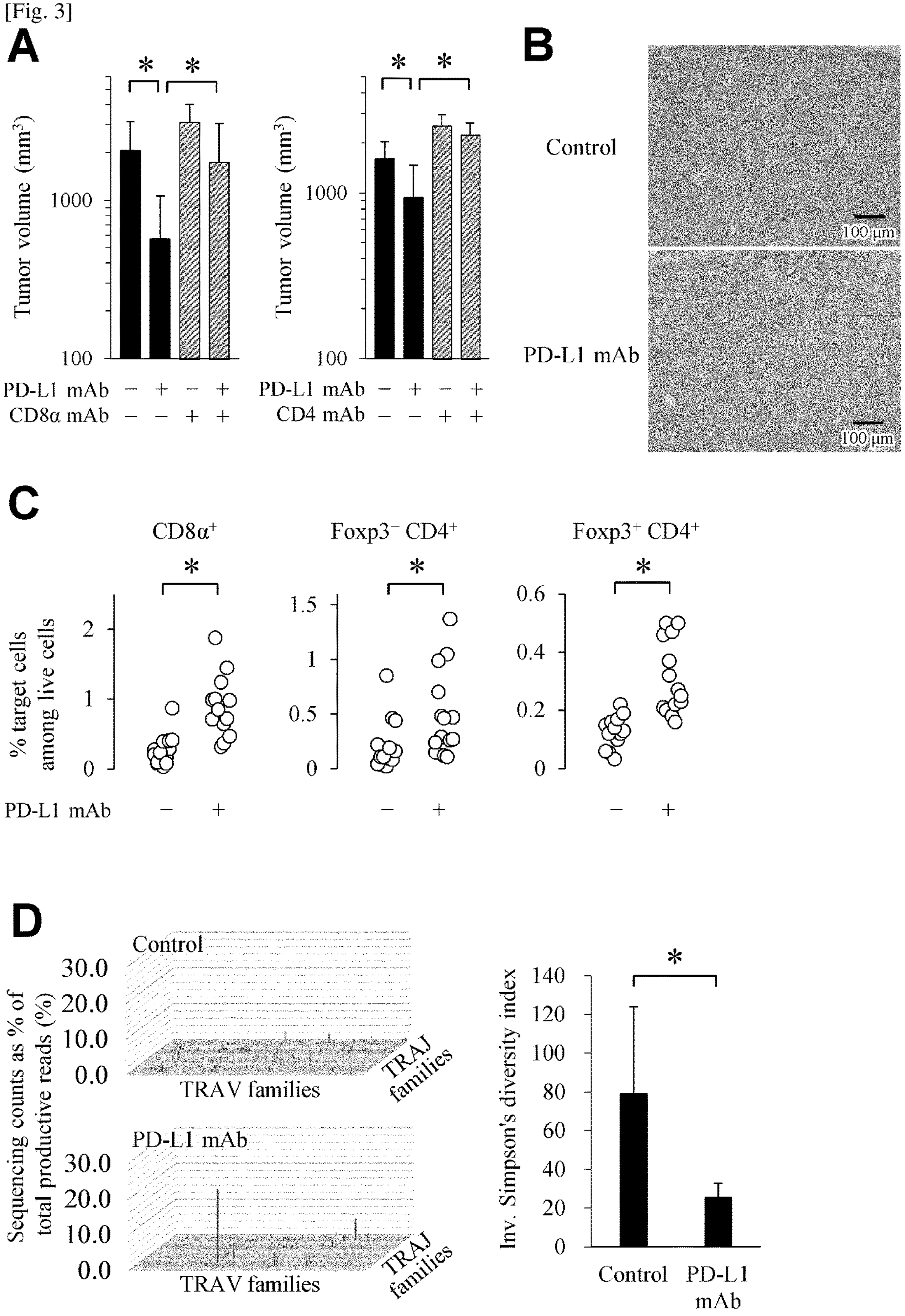

[Fig. 4]
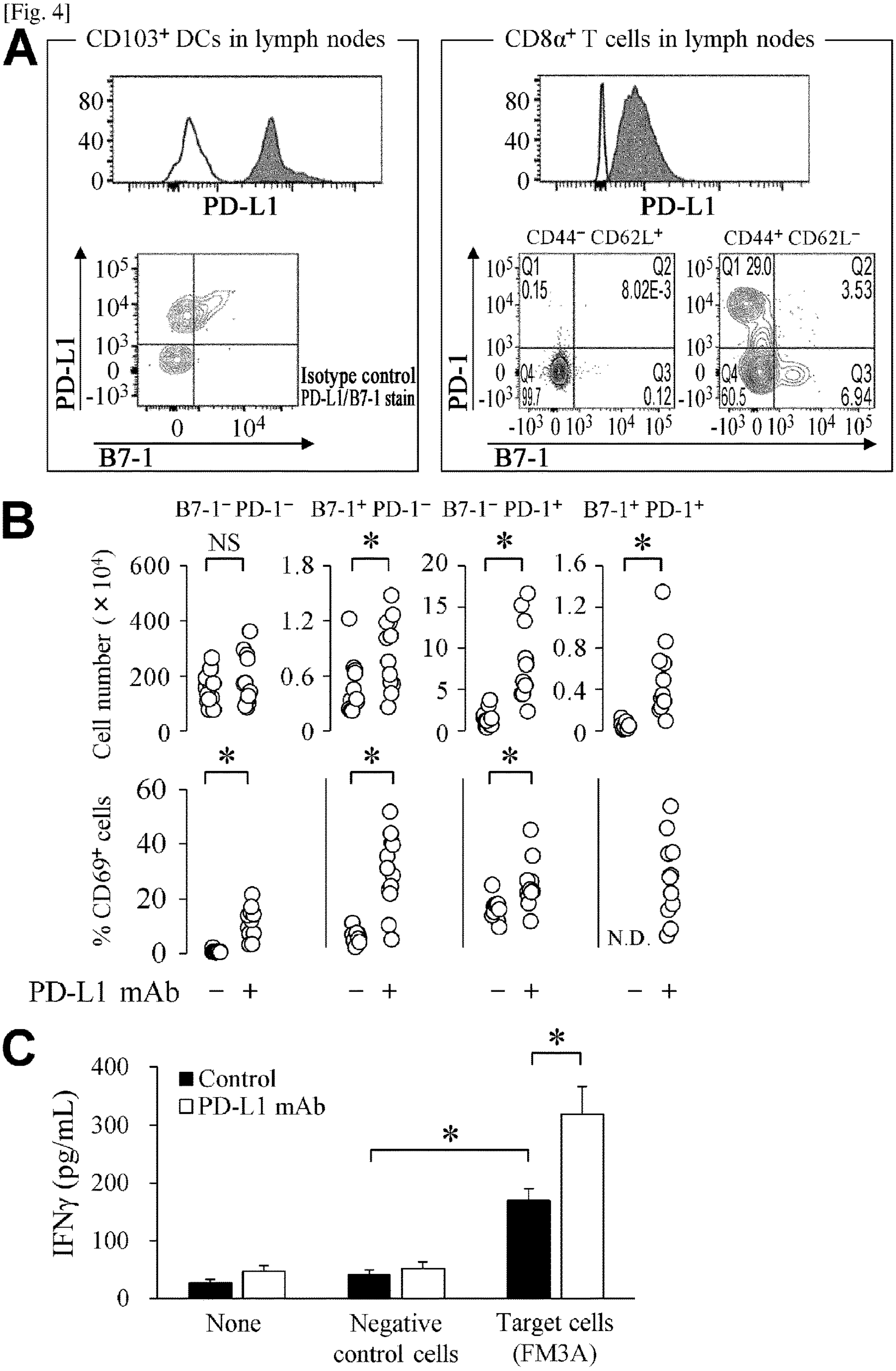

[Fig. 5]
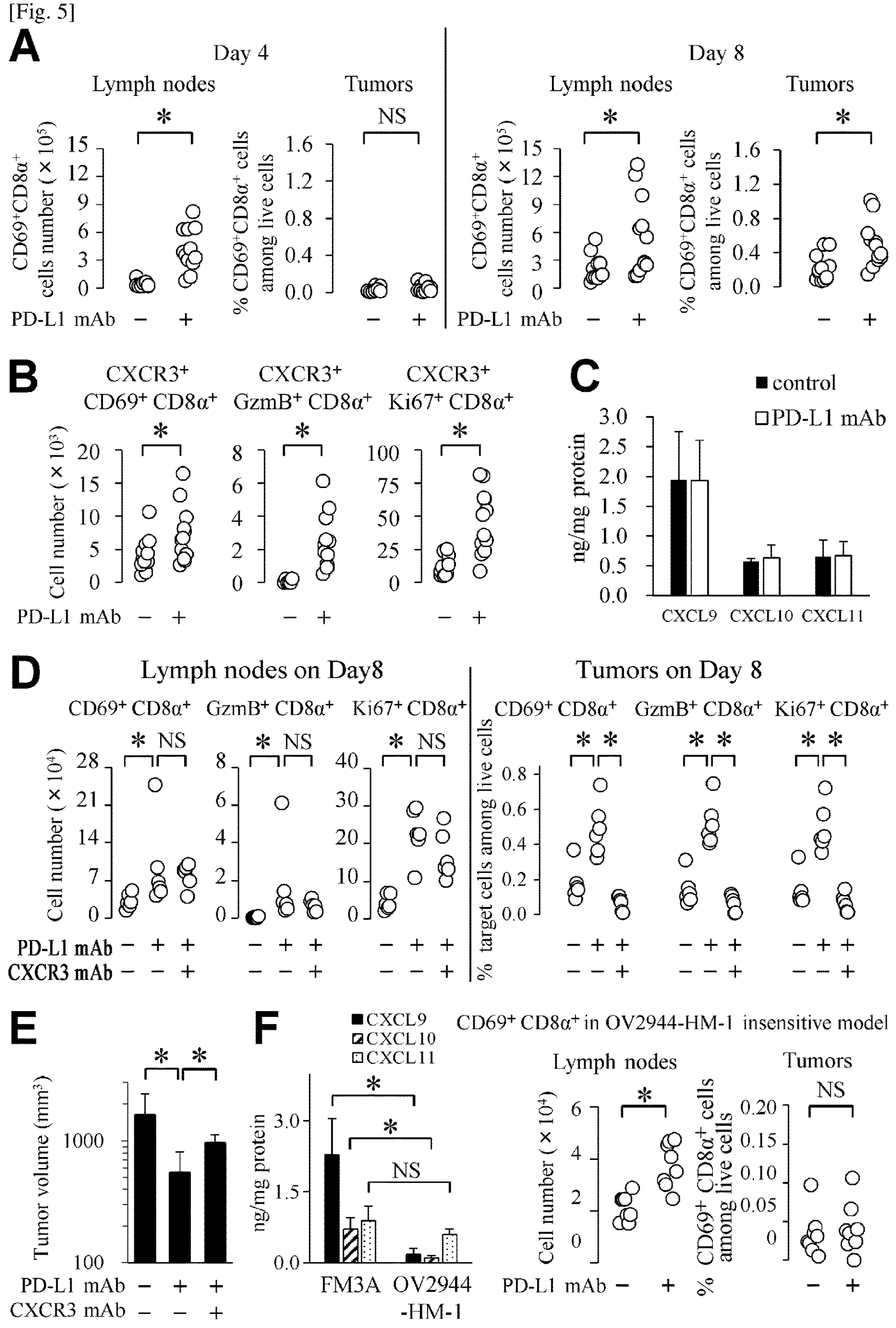

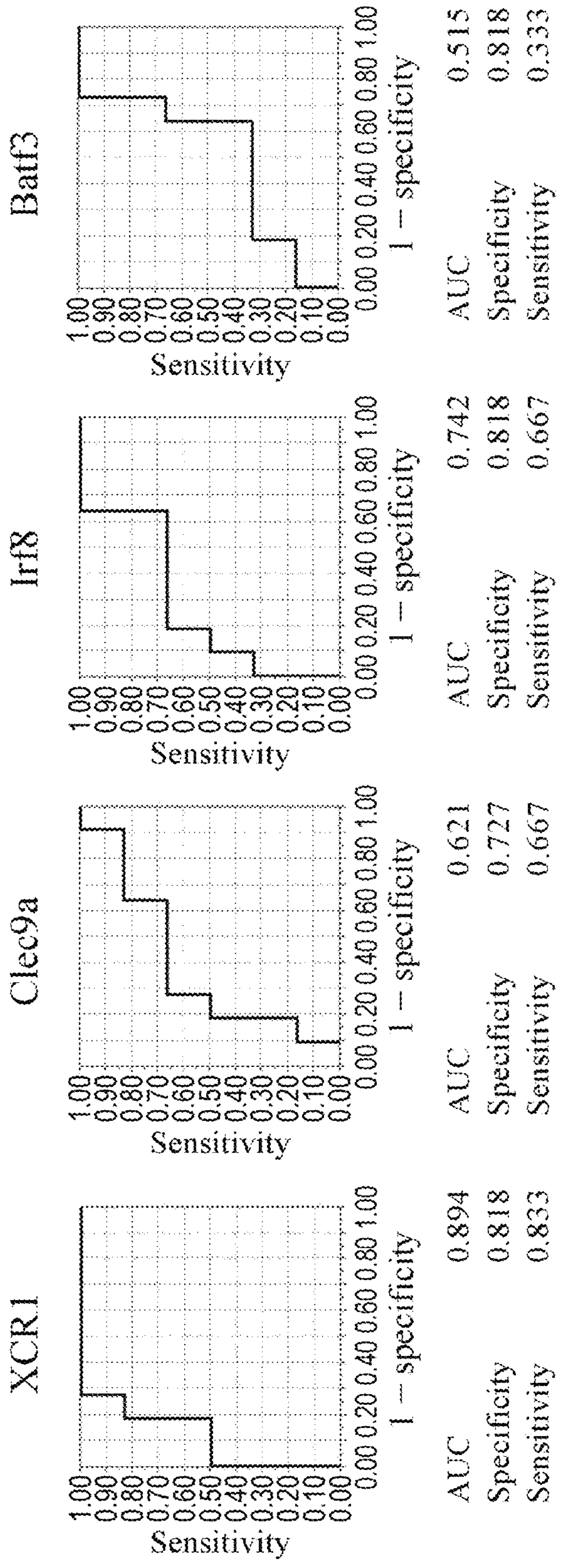
[Fig. 6A]

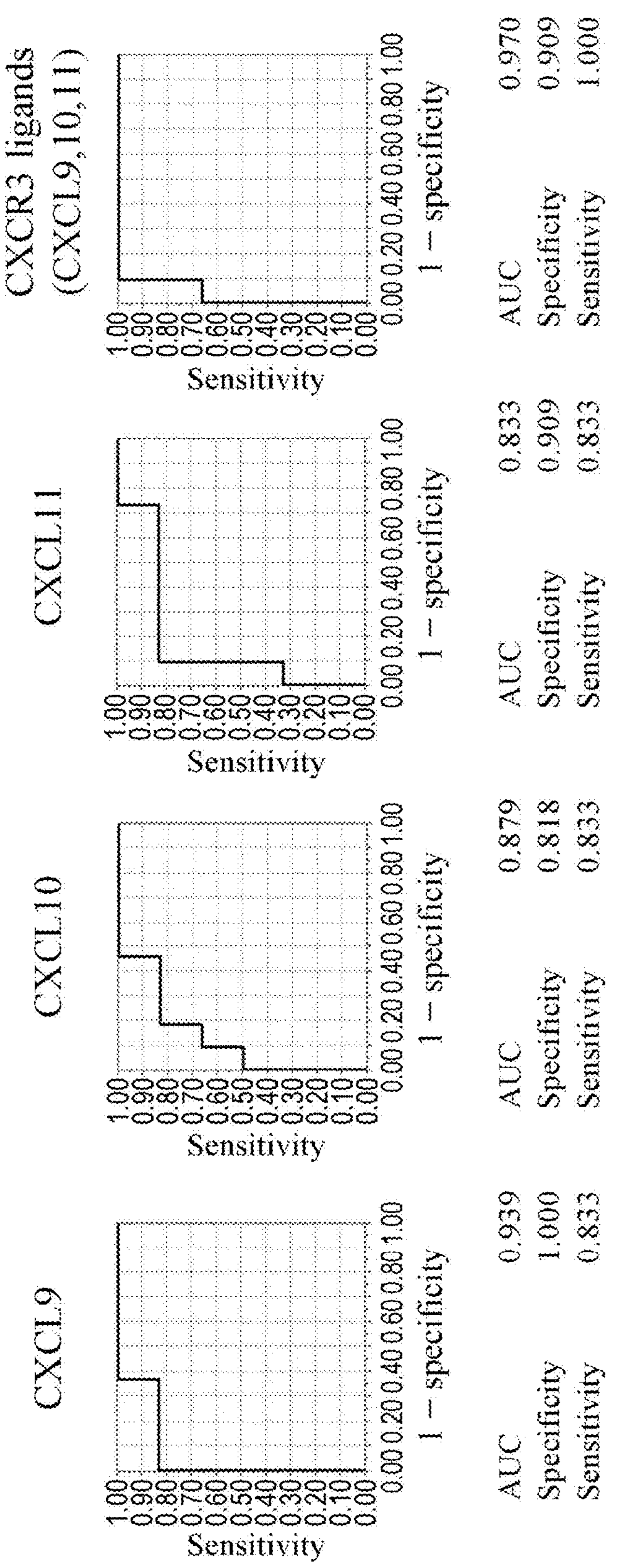
[Fig. 6B]

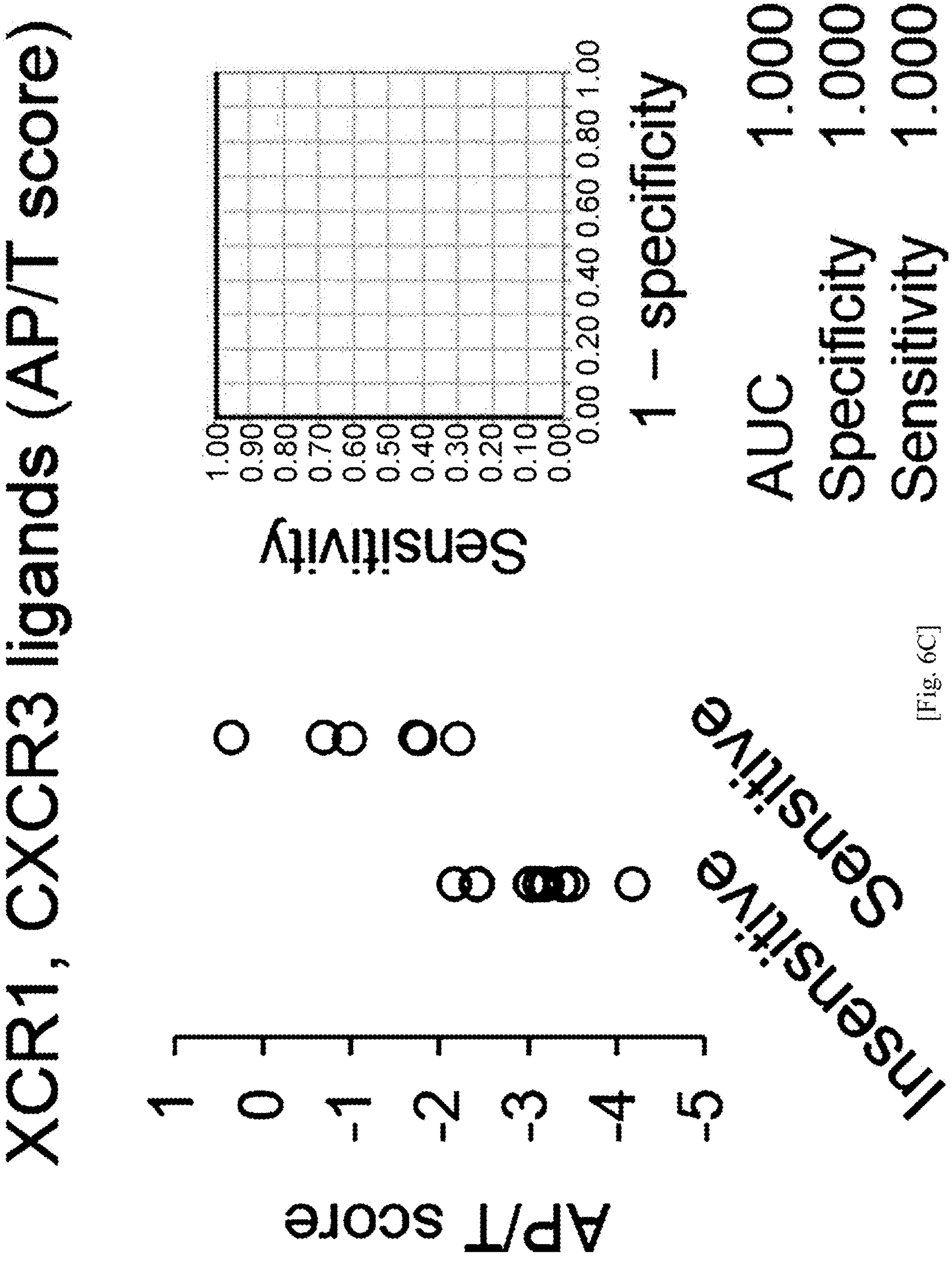
[Fig. 6C]

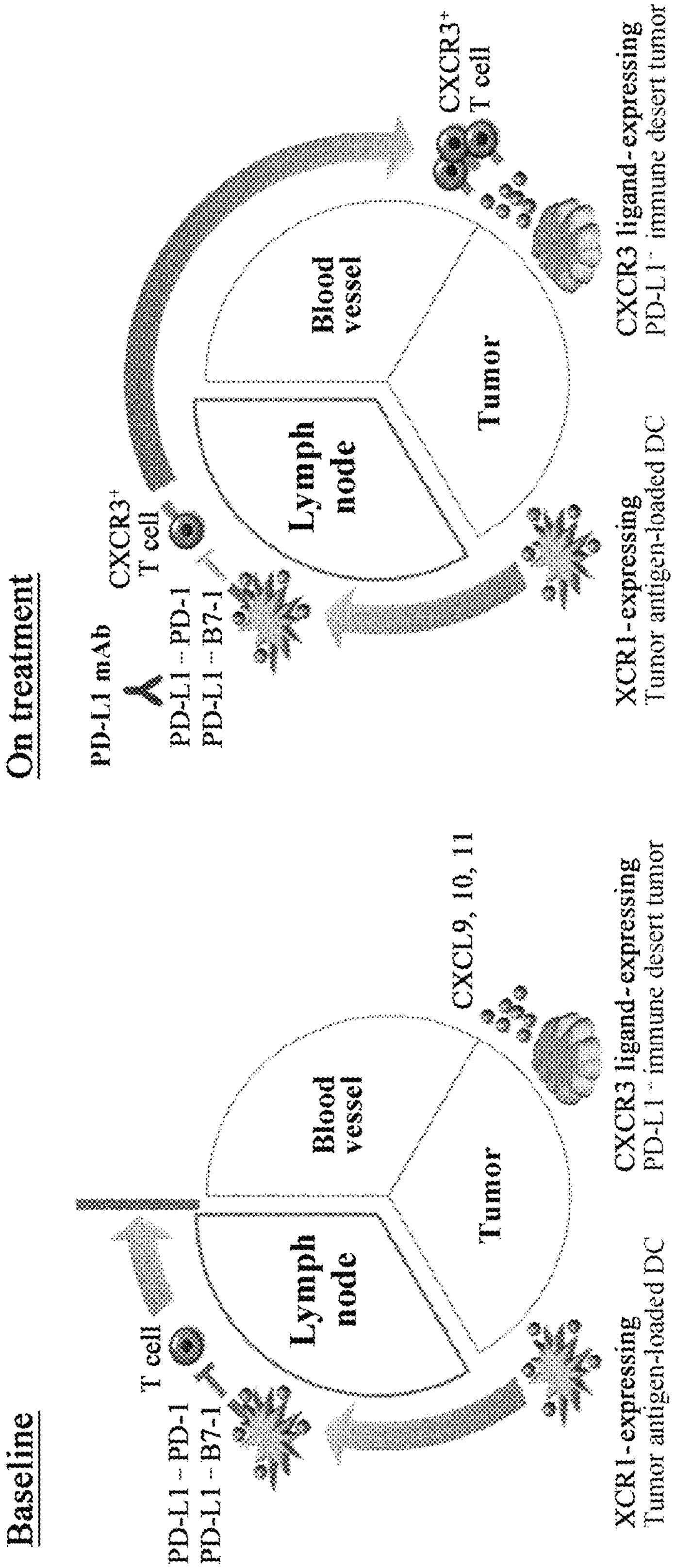
[Fig. 6D]

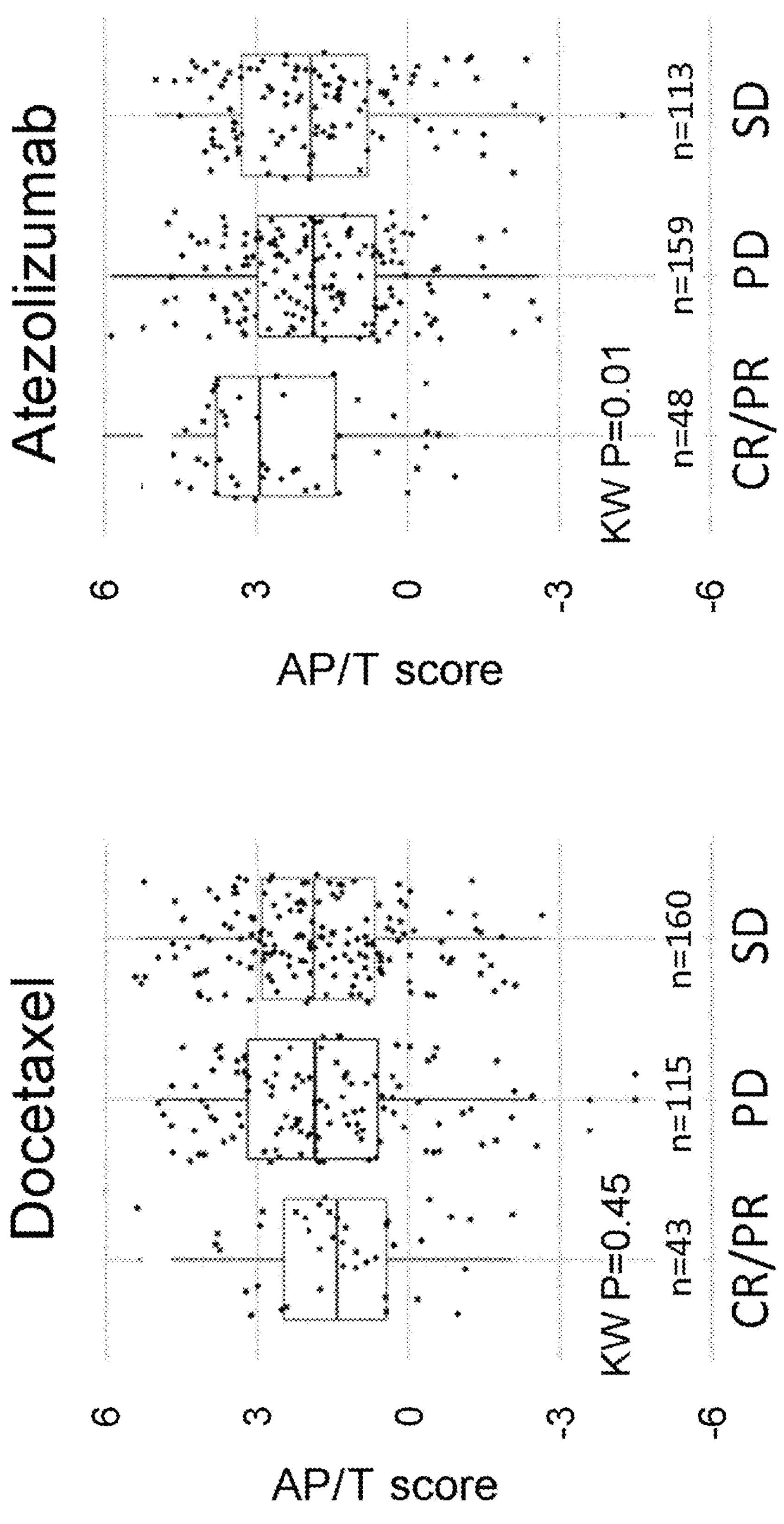
[Fig. 7A]

| AP/T score cut-off points | N (%) | HR | 95% CI | P-value |
|---|---|---|---|---|
| 30th percentile (Top 70%) | 509(70) | 0.77 | 0.62-0.95 | 0.014 |
| 50th percentile (Top 50%) | 364(50) | 0.76 | 0.59-0.97 | 0.031 |
| 70th percentile (Top 30%) | 218(30) | 0.71 | 0.51-0.99 | 0.045 |
| BEP | 727(100) | 0.84 | 0.71-1 | 0.056 |
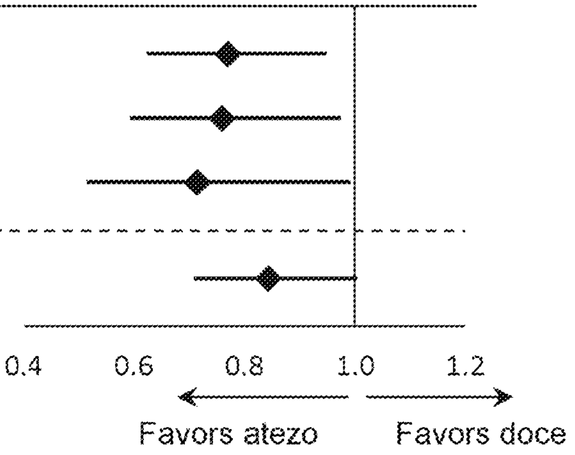
[Fig. 7B]

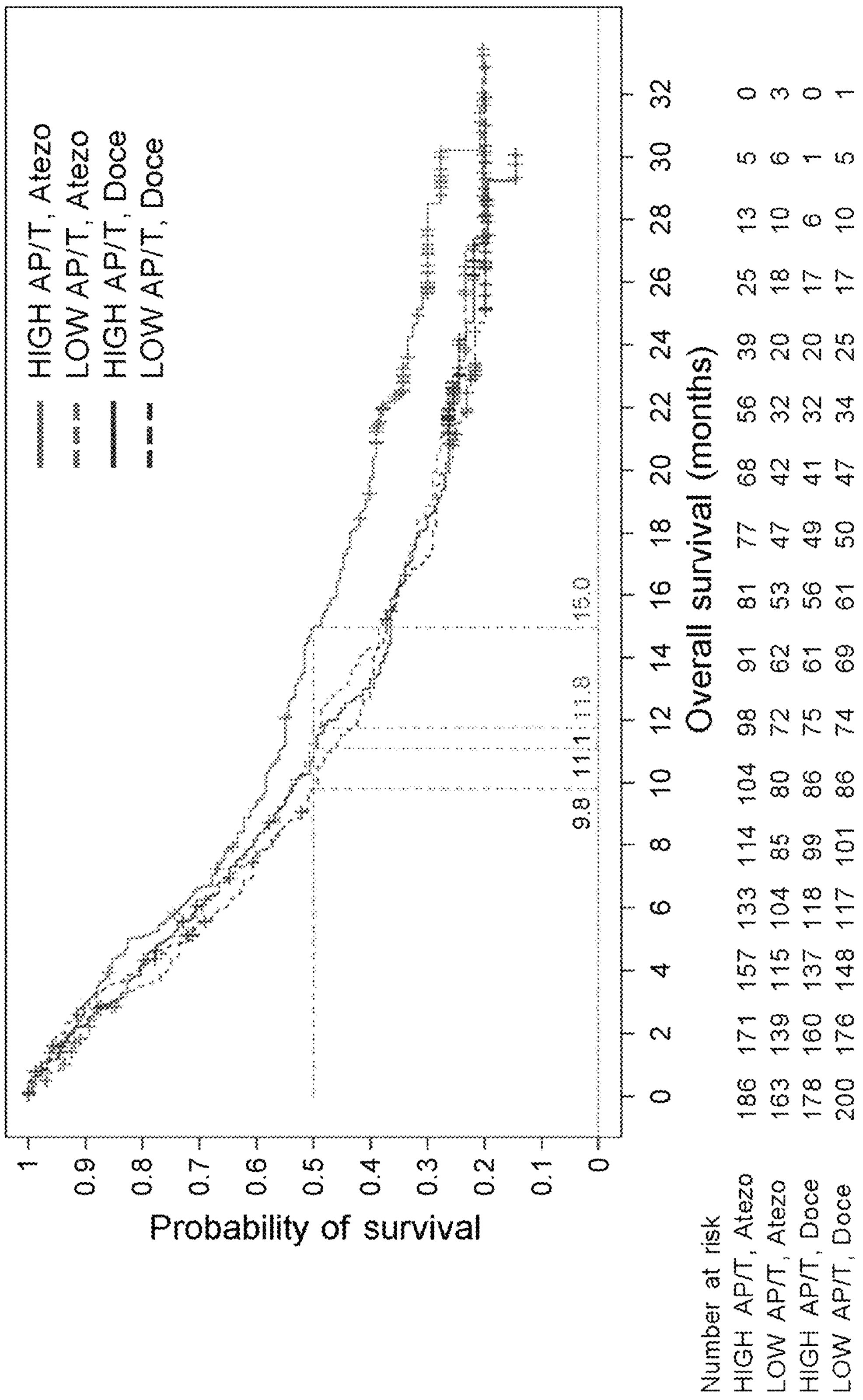
[Fig. 7C]

| | | mOS | | | | |
|---|---|---|---|---|---|---|
| Population | N (%) | Atezo | Doce | HR | 95% CI | P-value |
| HIGH AP/T | 364(50) | 15.0 | 11.1 | 0.76 | 0.59-0.97 | 0.031 |
| LOW AP/T | 363(50) | 11.8 | 9.8 | 0.95 | 0.75-1.22 | 0.713 |
| BEP | 727(100) | 12.8 | 10.3 | 0.84 | 0.71-1.00 | 0.056 |
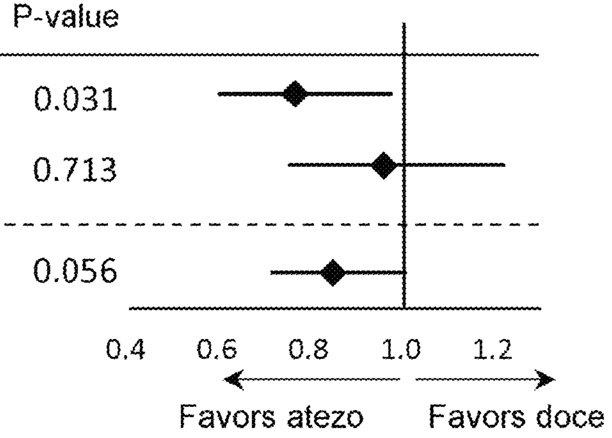
[Fig. 7D]

BIOMARKERS FOR PREDICTING THE RESPONSE TO CHECKPOINT INHIBITORS

CROSS-REFERENCE TO RELATED APPLICATIONS

This application is the National Stage of International Application No. PCT/JP2021/011302, filed on Mar. 19, 2021, which claims the benefit of Japanese Application No. 2020-0048845, filed on Mar. 19, 2020. The contents of the International Application are hereby incorporated by reference in their entirety.

Sequence Listing

This application contains a Sequence Listing that has been submitted electronically as an ASCII text file named SequenceListing.txt. The ASCII text file, created on Sep. 16, 2022, is 23,437 bytes in size. The material in the ASCII text file is hereby incorporated by reference in its entirety.

TECHNICAL FIELD

The invention provides biomarkers for predicting the response to checkpoint inhibitors.

BACKGROUND ART

Programmed Death Ligand 1 (PD-L1) plays a major role in suppressing the host's antitumor immune response (NPL1). Interaction between PD-L1 on cancer cells or tumor-infiltrating immune cells with its receptors, PD-1 and B37-1 (also known as CD80), on T cells delivers a signal that inhibits the activation of T cells (NPL2). PD-1/PD-L1 inhibitors generally show higher clinical benefit specifically in patients with high intratumoral PD-L1 expression. Interestingly, the phase 3 OAK trial (for non-small cell lung cancer) showed a survival advantage for atezolizumab (an anti-PD-L1 antibody which is one of the PD-1/PD-L1 inhibitors) versus docetaxel even in the subgroup with low or undetectable PD-L1 on tumor cells and immune cells (TC0/IC0) (NPL3). This result was consistent with the analysis of PD-L1 gene expression in tumor tissues (NPL3). The value of intratumoral PD-L1 expression in predicting a patient's response to such treatment is still less than perfect. Therefore, determining which patients derive benefit from PD-1/PD-L1-targeted therapy remains an important clinical question. For example, biomarkers for the conventional prediction of efficacy of the therapy have not been sufficiently optimized with regard to the types and combinations of markers for certain purposes (PTL 1 to 9). On the other hand, PD-L1 is reported to be expressed also on dendritic cells (DCs) in tumor-draining lymph nodes of patients with cancer (NPL4). PD-1 is reported to be highly expressed on T cells not only in tumor tissue but also in lung tumor-draining lymph nodes (NPL5 and NPL6). In addition, PD-L1 was also reported to compete with CD28 for B7-1 binding on antigen-presenting cells, suppressing T cell priming by outcompeting signaling through CD28/B7-1 (NPL7). However, the role of T cell priming in tumor lymph nodes in the mechanism of action for PD-1/PD-L1-targeted therapy has not yet been clarified.

CITATION LIST

Patent Literature

PTL 1: US 2015/0071910
PTL 2: WO 2015/120382
PTL 3: WO 2016/168133
PTL 4: WO 2017/013436
PTL 5: WO 2017/176925
PTL 6: WO 2018/209324
PTL 7: WO 2018/231771
PTL 8: WO 2018/225063
PTL 9: WO 2018/055145

Non Patent Literature

NPL 1: Zou W, Wolchok J D, Chen L., Science translational medicine 2016; 8(328):328rv4
NPL 2: Butte M J, Keir M E, Phamduy T B, Sharpe A H, Freeman G J., Immunity 2007; 27(1):111-22
NPL 3: Rittmeyer A, Barlesi F, Waterkamp D, Park K, Ciardiello F, von Pawel J, et al., Lancet (London, England) 2017; 389(10066):255-65
NPL 4: Curiel T J, Wei S, Dong H, Alvarez X, Cheng P, Mottram P, et al., Nature medicine 2003; 9(5):562-7
NPL 5: Gros A, Robbins P F, Yao X, Li Y F, Turcotte S, Tran E, et al., The Journal of clinical investigation 2014; 124(5):2246-59
NPL 6: van de Ven R, Niemeijer A N, Stam A G M, Hashemi S M S, Slockers C G, Daniels J M, et al., ERJ open research 2017; 3(2)
NPL 7: Butte M J, Pena-Cruz V, Kim M J, Freeman G J, Sharpe A H, Molecular immunology 2008; 45(13):3567-72

SUMMARY OF INVENTION

Technical Problem

In the conventional methods of predicting the efficacy of PD-1/PD-L1 inhibitors (such as anti-PD-1 antibodies or anti-PD-L1 antibodies), the biomarkers include intratumoral expression levels of PD-1 and PD-L1 which are the targets of the inhibitors, and indicators showing that immune activation (such as activation of the IFN-gamma pathway) has already been manifested using tumor samples. However, if PD-1, PD-L1, or IFN-gamma is used as a marker, patients in whom immune activation has already been occurred in tumors at the time of drug administration can be mainly selected, and one can fail to identify potential patients who are expected to be responsive to a PD-1/PD-L1 inhibitor, in which PD-1 or PD-L1 has been expressed at a low level or has not been expressed, or the IFN-gamma pathway has not been activated, but the activation has been prepared in draining lymph nodes.

Solution to Problem

The present invention is based on the concept that the main action mechanism of PD-1/PD-L1 inhibitors is the inhibition of the binding between PD-1 and PD-L1. In view of this, PD-1/PD-L1 inhibitors such as anti-PD-1 antibodies and anti-PD-L1 antibodies are expected to provide clinical benefit even in the subgroup of cancer patients where PD-L1 is low or undetectable on tumor cells and immune cells. The inventors investigated the mechanism of action by which PD-L1-negative tumors respond to PD-1/PD-L1-targeted therapy. As a result, the inventors found predictive biomarkers based on the mechanism of action, which are expected to be useful in determining which patients stand to benefit from PD-1/PD-L1-targeted therapy.

Specifically, the combination of biomarkers of the present invention includes both the presence of dendritic cells (DCs)

that have tumor antigen-presenting ability and the presence of chemokine that accumulates activated T cells in tumor. By detecting this combination, rather than either one of the two markers, it is possible to detect the stage of preparation in lymph nodes, and increase the accuracy of the prediction of patient's responsiveness to the therapy. Exclusion of the markers for T cell activation, such as PD-L1 and IFN-gamma in the current gene set may reduce too much stress on patients with pre-activated immunity. Of note, the proposed gene sets combining antigen-presenting ability and T cell recruitment may enable the selection of responder patients both with/without pre-activated immunity, which is also referred to as "inflamed tumor/immune-desert tumor".

More specifically, the present invention provides the following.

[1] A method of identifying a patient who has or is suspected of having a cancer which is responsive to a therapy comprising administration of an effective amount of a PD-1/PD-L1 inhibitor, wherein the method comprises:

detecting (i) and (ii) below in a sample from the patient:

(i) at least one marker for estimating an intratumoral amount of dendritic cells (DCs) having cross-presentation ability to CD8-positive T cells; and (ii) at least one chemokine that accumulates effector T cells in tumor.

[1a] A method of identifying a patient who has or is suspected of having a cancer which is responsive to a therapy comprising administration of an effective amount of a PD-1/PD-L1 inhibitor (which may be a PD-1 inhibitor or PD-L1 inhibitor that can inhibit binding between PD-1 and PD-L1, such as an anti-PD-1 antibody or anti-PD-L1 antibody; the same applies to other embodiments disclosed herein), wherein the method comprises:

detecting (i) and (ii) below in a sample from the patient:

(i) at least one marker which is an antigen-presenting cell marker or an antigen presentation marker; and (ii) at least one chemokine or chemoattractant.

[2] The method of [1] or [1a], wherein the therapy comprises administration of an effective amount of an anti-PD-L1 antibody.

[3] The method of any one of [1], [1a], and [2], wherein the therapy comprises administration of an effective amount of atezolizumab.

[4] The method of any one of [1] to [3], wherein the cancer is selected from the group consisting of: non-small cell lung cancer, small cell lung cancer, breast cancer, bladder cancer, and alveolar soft part sarcoma.

[5] The method of any one of [1] to [4], wherein each marker is not a T cell activation marker.

[6] The method of any one of [1] to [5], wherein the at least one marker is one, two, three, four, five, six, or all of: XCR1, Clec9, Irf8, Batf3, CD205, CD103, and CD141.

[7] The method of any one of [1] to [6], wherein the at least one marker is XCR1.

[8] The method of any one of [1] to [7], wherein the at least one chemokine is a CXCR3 ligand.

[9] The method of any one of [1] to [8], wherein the at least one chemokine is one, two, or all of: CXCL9, CXCL10, and CXCL11.

[10] The method of any one of [1] to [9], wherein the at least one chemokine is all of: CXCL9, CXCL10, and CXCL11.

[11] The method of any one of [1] to [10], wherein said detecting (i) is measuring a mRNA expression level of the marker, and wherein said detecting (ii) is measuring a mRNA expression level of the chemokine.

[12] The method of any one of [1] to [11], wherein said detecting (i) and (ii) is measuring an average of mRNA expression levels of the marker and one or more chemokines.

[13] The method of [12], wherein the marker is XCR1, and the one or more chemokines are selected from CXCL9, CXCL10, and CXCL11.

[14] The method of [13], wherein the chemokines are all of CXCL9, CXCL10, and CXCL11.

[15] A method of predicting the therapeutic effect of a PD-1 inhibitor or PD-L1 inhibitor on a cancer patient, wherein the method comprises:

detecting (i) and (ii) below in a sample from the patient:

(i) at least one marker for estimating an intratumoral amount of dendritic cells (DCs) having cross-presentation ability to CD8-positive T cells; and (ii) at least one chemokine that accumulates effector T cells in tumor.

Furthermore, the present invention provides the following.

[16] The method of [1] or [2], wherein the therapy comprises administration of an effective amount of a humanized anti-PD-L1 antibody.

[17] The method of any one of [1] to [16], wherein the cancer is lung cancer.

[18] The method of any one of [1] to [16], wherein the cancer is non-small cell lung cancer.

[19] The method of any one of [1] to [18], wherein the sample is a lung tissue sample.

[20] The method of any one of [1] to [6], wherein the at least one marker is one, two, three, or all of: XCR1, Clec9, Irf8, and Batf3.

[21] The method of any one of [1] to [12], wherein said detecting (i) and (ii) is determining an average (AP/T score) of (a) and (b) below: (a) a mRNA expression level of the marker; and (b) an mRNA expression level(s) of one or more chemokine.

[22] The method of [13] or [21], wherein the method further comprises determining whether the average (AP/T score) is equal to or more than a threshold value.

[23] The method of [22], wherein the method further comprises identifying the patient as a patient on whom the therapy is conducted, if the average (AP/T score) is equal to or more than a threshold value.

[24] The method of [23], wherein the method further comprises determining that the therapy is conducted on the patient.

[25] The method of [24], wherein the method further comprises conducting the therapy on the patient.

[26] The method of [25], wherein the method comprises administering an effective amount of the PD-1/PD-L1 inhibitor to the patient.

[27] A method of treating, in a patient, a cancer which is responsive to a therapy comprising administration of an effective amount of a PD-1/PD-L1 inhibitor, wherein the method comprises:

obtaining a tissue sample from a human having or suspected of having cancer;

detecting (i) and (ii) below in said sample;

(i) at least one marker for estimating an intratumoral amount of dendritic cells (DCs) having cross-presentation ability to CD8-positive T cells; and (ii) at least one chemokine that accumulates effector T cells in tumor;

identifying a patient who has or is suspected of having a cancer which is responsive to the therapy; or determining that the therapy is conducted on the patient; and administering an effective amount of the inhibitor to the patient.

[28] A method of detecting (i) and (ii) below in a sample from a subject:

(i) at least one marker for estimating an amount of dendritic cells (DCs) having cross-presentation ability to CD8-positive T cells; and (ii) at least one chemokine that accumulates effector T cells.

[29] A method of selecting a patient who has or is suspected of having a cancer which is responsive to a therapy comprising administration of an effective amount of a PD-1/PD-L1 inhibitor, wherein the method comprises:

determining a patient group consisting of patients who have or are suspected of having a cancer;

measuring an average (AP/T score) of (i) and (ii) below in a sample from each patient in the patient group:

(i) a mRNA expression level of a marker for estimating an intratumoral amount of dendritic cells (DCs) having cross-presentation ability to CD8-positive T cells; and (ii) a mRNA expression level(s) of one or more chemokines that accumulate effector T cells in tumor;

determining a threshold value such that a certain percentage of the total patients in the patient group have the average (AP/T score) which is equal to or more than the threshold value; and selecting a patient with the average (AP/T score) which is equal to or more than the threshold value.

[30] A method of predicting the therapeutic effect of a PD-1/PD-L1 inhibitor on a cancer patient in a patient group, wherein the method comprises:

determining a patient group consisting of patients who have or are suspected of having a cancer;

measuring an average (AP/T score) of (i) and (ii) below in a sample from each patient in the patient group:

(i) a mRNA expression level of at least one marker for estimating an intratumoral amount of dendritic cells (DCs) having cross-presentation ability to CD8-positive T cells; and (ii) a mRNA expression level(s) of one or more chemokines that accumulate effector T cells in tumor;

determining a threshold value such that a certain percentage of the total patients in the patient group have the average (AP/T score) which is equal to or more than the threshold value; and showing that the therapeutic effect of the inhibitor is high on a patient with the average (AP/T score) which is equal to or more than the threshold value.

[31] A pharmaceutical composition for treating a subject having cancer comprising a PD-1/PD-L1 inhibitor, wherein the subject is identified/predicted/treated/detected/selected by the method according to any one of [1] to [30], wherein the method can predict the therapeutic effect of a PD-1/PD-L1 inhibitor on a cancer patient in a patient group.

[32] A kit comprising means for performing the method according to any one of [1] to [30] and instructions for use.

[33] Use of one or more mRNAs and/or protein-specific probes for the manufacture of a kit for predicting sensitivity of the therapy that administers a PD-1/PD-L1 inhibitor to an individual suffering from cancer, said kit being used to perform the method according to any one of [1] to [30].

BRIEF DESCRIPTION OF DRAWINGS

FIG. 1 shows the relationship between antitumor activity of anti-PD-L1 monoclonal antibody (mAb) and PD-L1 expression (Examples 1 and 2). (A) Representative tumor growth curves: Mice bearing tumors were randomly divided into groups. Solid line, control; dotted line, PD-L1 mAb 10 mg/kg. Data are shown as the mean+SD (n=5-15/group). Statistical analysis used Wilcoxon rank sum test; *, P<0.05; NS, not significant. (B) PD-L1 mRNA expression in tissues insensitive or sensitive to PD-L1 mAb (left), and ROC curve analysis (right). Shaded circle indicates results for the FM3A model.

FIG. 2 shows PD-L1 expression and CD8 alpha+ T cell infiltration in FM3A tumor model (Example 2). (A) PD-L1 immunostaining in tumor tissue at baseline in Colon 38 model (positive control) and FM3A model. (B) CD8 alpha immunostaining in tumor tissue at baseline. (C) PD-L1 expression on tumor-infiltrating immune cells and tumor cells in FM3A tumors. (D) Distribution of cells in FM3A tumors. Cells were determined by flow cytometric analysis (C, D).

FIG. 3 shows that anti-PD-L1 mAb increases specific T cells in tumor, resulting in T cell-dependent antitumor activity in the PD-L1-negative tumor model (Example 3). (A) Tumor volume of mice treated with PD-L1 mAb along with CD8 alpha mAb or CD4 mAb in the FM3A tumor model (n=7/group, Day 19). Data are shown as the mean+SD. Statistical analysis used Wilcoxon rank sum test and the Holm-Bonferroni method; *, P<0.05. (B) Infiltration of CD8 alpha+ T cells into tumors was determined by CD8 alpha immunostaining in tumor tissue after PD-L1 mAb treatment (Day 19). (C) Percentage of each type of T cells in tumor after PD-L1 mAb treatment (Day 19) (n=14/group). Cells were determined by flow cytometric analysis. Statistical analysis used Wilcoxon rank sum test; *, P<0.05. (D) Percentage of T cell receptor alpha (TCR alpha) sequences in tumor after PD-L1 mAb treatment (Day 19). Next-generation sequencing was performed with unbiased TCR repertoire analysis technology. The inverse of Simpson's diversity index was used to examine diversity based on the clonal dominance of each TCR clonotype (n=3-5/group). Data are shown as the mean+SD.

FIG. 4 shows the role of PD-L1 in T cell priming in lymph nodes (Example 3). (A) PD-L1 expression or PD-L1 receptors (PD-1 and B7-1) expression on antigen-presenting dendritic cells (DCs) or CD8 alpha+ T cells in lymph nodes at baseline. (B) Number of PD-L1 receptors (PD-1 and B7-1)+CD8 alpha+ T cells and the frequency of CD69+ cells among each PD-L1 receptors+CD8 alpha+ T cells in lymph nodes after PD-L1 mAb treatment (Day 4) (n=12/group). Statistical analysis used Wilcoxon rank sum test; *, P<0.05; NS, not significant. (C) Secretion of IFN gamma after specific stimulation of lymphocytes by co-culturing with tumor cells (n=3/group). IFN gamma was quantified by ELISA. Statistical analysis used Student's t test and the Holm-Bonferroni method; *, P<0.05. Data are shown as the mean+SD.

FIG. 5 shows time lag between the increase in activated CD8 alpha+ T cells in lymph nodes and the increase in the tumor is caused by T cell trafficking to a TC0/IC0 tumor (Example 4). (A) Time course of CD8 alpha+ T cells activation in tumor draining lymph nodes and in tumor after PD-L1 mAb treatment in the FM3A model (Day 4, 8) (n=12/group). (B) Number of CXCR3+ activated CD8 alpha+ T cells in lymph nodes after PD-L1 mAb treatment (n=12/group). (C) Expression of CXCR3 ligands in tumor (n=6/group). (D) Number of activated CD8 alpha+ T cells in lymph nodes and in tumors after PD-L1 mAb treatment (Day 8) (n=6/group). (E) Tumor volume of mice treated with PD-L1 mAb along with anti-CXCR3 mAb in the FM3A tumor model. (Day 18) (n=6/group). (F) Expression of CXCR3 ligands in tumors of FM3A and OV2944-HM-1 (left). Number of activated CD8 alpha+ T cells in lymph nodes (middle) and in tumors (right) after PD-L1 mAb treatment (Day 8) (n=8/group). Data are shown as the mean+SD. Statistical analysis used Wilcoxon rank sum test and the Holm-Bonferroni method; *, P<0.05; NS, not significant.

FIG. 6 (FIGS. 6A to 6D) shows the relationship between antitumor activity of anti-PD-L1 mAb and antigen-presenting DC-related gene expression and/or gene expression of CXCR3 ligands in murine tumor models (Examples 3 and 5). FIG. 6A shows ROC curve analysis by expression of antigen-presenting DC-related genes.

FIG. 6B shows ROC curve analysis by expression of CXCR3 ligands.

FIG. 6C shows the combined RNA expression of XCR1 three CXCR3 ligands ("AP/T scores") in PD-L1 mAb-insensitive or -sensitive tumor tissues and ROC curve analysis.

FIG. 6D shows hypothesis for mechanism of action of anti-PD-L1 Ab in the PD-L1-negative and immune desert-like tumor model based on the cancer-immunity cycle.

FIG. 7 shows association of clinical outcome and the combined mRNA expression levels of XCR1, CXCL9, CXCL10 and CXCL11 ("AP/T scores") in tumor tissue in the phase III OAK trial (Example 6). FIG. 7A shows relation between ORR and AP/T scores.

FIG. 7B shows a forest plots of HEs for OS in the BEP population and AP/T scores above the 30th, 50th, 70th percentile cut-points.

FIGS. 7C and 7D show Kaplan-Meier estimates and forest plots of HRs for OS in the HIGH and LOW AP/T score subgroups (cut at 50th percentile) in the atezolizumab and docetaxel treatment arms.

FIGS. 7C and 7D show Kaplan-Meier estimates and forest plots of HRs for OS in the HIGH and LOW AP/T score subgroups (cut at 50th percentile) in the atezolizumab and docetaxel treatment arms.

DESCRIPTION OF EMBODIMENTS

The techniques and procedures described or referenced herein are generally well understood and commonly employed using conventional methodology by those skilled in the art, such as, for example, the widely utilized methodologies described in Sambrook et al., Molecular Cloning: A Laboratory Manual 3d edition (2001) Cold Spring Harbor Laboratory Press, Cold Spring Harbor, N.Y.; Current Protocols in Molecular Biology (F. M. Ausubel, et al. eds., (2003)); the series Methods in Enzymology (Academic Press, Inc.): PCR 2: A Practical Approach (M. J. MacPherson, B. D. Hames and G. R. Taylor eds. (1995)), Harlow and Lane, eds. (1988) Antibodies, A Laboratory Manual, and Animal Cell Culture (R. I. Freshney, ed. (1987)); Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney), ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-8) J. Wiley and Sons; Handbook of Experimental Immunology (D. M. Weir and C. C. Blackwell, eds.); Gene Transfer Vectors for Mammalian Cells (J. M. Miller and M. P. Calos, eds., 1987); PCR: The Polymerase Chain Reaction, (Mullis et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: A Practical Approach (D. Catty., ed., IRL Press, 1988-1989); Monoclonal Antibodies: A Practical Approach (P. Shepherd and C. Dean, eds., Oxford University Press, 2000); Using Antibodies: A Laboratory Manual (E. Harlow and D. Lane (Cold Spring Harbor Laboratory Press, 1999); The Antibodies (M. Zanetti and J. D. Capra, eds., Harwood Academic Publishers, 1995); and Cancer: Principles and Practice of Oncology (V. T. DeVita et al., eds., J. B. Lippincott Company, 1993).

Unless defined otherwise, technical and scientific terms used herein have the same meaning as commonly understood by one of ordinary skill in the art to which this invention belongs. Singleton et al., Dictionary of Microbiology and Molecular Biology 2nd ed., J. Wiley & Sons (New York, N.Y. 1994), and March, Advanced Organic Chemistry Reactions, Mechanisms and Structure 4th ed., John Wiley & Sons (New York, N.Y. 1992), provide one skilled in the art with a general guide to many of the terms used in the present application. All references cited herein, including patent applications and publications, are incorporated by reference in their entirety.

Programmed cell death protein 1 (PD-1; also known as CD274 or B7-H1) is a type I membrane protein which belongs to the CD28/CTLA-4 family of T cell regulators. PD-1 has two ligands, i.e., PD-L1 and PD-L2 which belong to the B7 family. It is thought that PD-1 with the ligands negatively regulate immune responses such as T cell responses. PD-L1 and PD-1 are highly expressed in several types of cancers, and thought to have a role in cancer immune evasion. Inhibitors such as "(immune) checkpoint inhibitors" which inhibit, for example, the interaction between PD-1 and PD-L1 can enhance T-cell responses and increase antitumor activity.

The term "antibody" herein is used in the broadest sense and encompasses various antibody structures, including but not limited to monoclonal antibodies, polyclonal antibodies, multispecific antibodies (e.g., bispecific antibodies), chimeric antibodies, humanized antibodies, human antibodies, and antibody fragments thereof, so long as they exhibit the desired antigen-binding activity.

Herein, "PD-1/PD-L1 axis inhibitor" refers to a molecule that inhibits interaction between a PD-1/PD-L1 axis binding partner with another binding partner, and eliminates T-cell dysfunction due to signaling on the PD-1/PD-L1 axis, and thus enhances T-cell function such as cytotoxicity and cytokine generation. The term "PD-1/PD-L1 inhibitor" refers to a molecule that can inhibit interaction between PD-1 and PD-L1, and eliminates T-cell dysfunction due to signaling on the PD-1/PD-L1 axis, and thus enhances T-cell function such as cytotoxicity and cytokine generation. The PD-1/PD-L1 inhibitors include, for example, PD-L1 inhibitors and PD-1 inhibitors.

Herein, "PD-1 inhibitor" refers to a molecule that inhibits signal transduction due to interaction between PD-1 with a binding partner such as PD-L1. In some embodiments, the PD-1 inhibitor is an anti-PD-1 antibody.

Herein, "PD-L1 inhibitor" refers to a molecule that inhibits signal transduction due to interaction between PD-L1 and a binding partner such as PD-1 and B37-1. In some embodiments, the PD-L1 inhibitor is an anti-PD-L1 antibody. In some embodiments, the anti-PD-L1 antibody is a humanized anti-PD-L1 antibody. In some embodiments, the anti-PD-L1 antibody is atezolizumab (Genentech; CAS Registry Number: 1422185-06-5). Atezolizumab is a humanized monoclonal antibody against PD-L1. Atezolizumab binds to PD-L1, and blocks its binding to and activation of PD-1 expressed on activated T cells, and enhances T cell-mediated immune responses. The Fc region of atezolizumab is modified so as not to induce antibody-dependent cytotoxicity (ADCC) or complement-dependent cytotoxicity (CDC). Atezolizumab has been approved for the treatment of non-small cell lung cancer, small cell lung cancer, breast cancer, and bladder cancer such as urothelial carcinoma, and shown to be effective for alveolar soft part sarcoma. See, e.g., the National Center Institute (NCI) Drug Dictionary by NCI at the National Institutes of Health of the United States.

The terms "anti-PD-L1 antibody" and "an antibody that binds to PD-L1" refer to an antibody that is capable of binding PD-L1 with sufficient affinity such that the antibody is useful as a diagnostic and/or therapeutic agent in targeting PD-L1. In one embodiment, the extent of binding of an anti-PD-L1 antibody to an unrelated, non-PD-L1 protein is less than about 10% of the binding of the antibody to PD-L1 as measured, e.g., by a radioimmunoassay (RIA). In certain embodiments, an antibody that binds to PD-L1 has a dissociation constant (Kd) of 1 micro M or less, 100 nM or less, 10 nM or less, 1 nM or less, 0.1 nM or less, 0.01 nM or less, or 0.001 nM or less (e.g. $10^{-8}$ M or less, e.g. from $10^{-8}$ M to $10^{-13}$ M, e.g., from $10^{-9}$ M to $10^{-11}$ M). In certain embodiments, an anti-PD-L1 antibody binds to an epitope of PD-L1 that is conserved among PD-L1 from different species. The same applies to other antigens such as PD-1. In preferred embodiments, the anti-PD-L1 antibody binds to human PD-L1, for which the information is shown in, e.g., UniProtKB: Q9NZQ7.1 (for example, the nucleotide and amino acid sequences are shown in SEQ ID NOs: 1 and 9, respectively).

The term "monoclonal antibody (mAb)" as used herein refers to an antibody obtained from a population of substantially homogeneous antibodies, i.e., the individual antibodies composing the population are identical and/or bind to the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "humanized antibody" refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation. Effector functions may be exhibited by effector T cells.

An "effective amount" of a drug, a pharmaceutical, a composition (e.g., pharmaceutical composition), or an agent (e.g., a therapeutic agent or a pharmaceutical formulation) refers to an amount effective, at dosages and for periods of time necessary, to achieve the desired therapeutic or prophylactic result such as cancer treatment.

In connection with the "effective amount", herein, "therapeutically effective amount" refers to an amount of a drug/pharmaceutical/agent to treat or prevent a disorder/disease in a patient. In some embodiments, when treating cancer or tumor, the therapeutically effective amount of the agent reduces the number of cancer cells and/or the tumor size; inhibits cancer cell infiltration into peripheral organs; inhibits tumor metastasis; inhibits tumor growth; ameliorates the symptoms associated with cancer. When using such cancer therapeutic agents, the efficacy or therapeutic effect of the therapy is evaluated by, e.g., the duration of survival, time to disease progression (TTP), the response rates (RR), duration of response, quality of life (QOL), etc.

A "patient", "subject", or "individual" (these terms may be interchangeably used) is preferably a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the patient/subject is a human. In some embodiments, the patient/subject is a patient/subject who has or is suspected of having a cancer which is responsive to a therapy comprising administration of an effective amount of a PD-1/PD-L1 inhibitor such as an anti-PD-1 antibody or anti-PD-L1 antibody.

As used herein, "therapy" or "treatment" (or grammatical variations thereof such as "treat" or "treating") refers to clinical intervention in an attempt to alter the natural course of the individual being treated, and can be performed either for prophylaxis or during the course of clinical pathology. Desirable effects of therapy/treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

In an aspect, the invention provides a method for treating a cancer which is responsive to a therapy comprising administration of an effective amount of a PD-1/PD-L1 inhibitor such as an anti-PD-1 antibody or anti-PD-L1 antibody. In one embodiment, the method comprises administering to a patient/subject having the cancer an effective amount of a PD-1/PD-L1 inhibitor such as an anti-PD-1 antibody or anti-PD-L1 antibody. In one such embodiment, the method further comprises administering to the patient/subject an effective amount of at least one additional therapeutic agent described herein. A "patient/subject" according to any of the embodiments herein may be a human.

Herein, "detection/detecting" refers to any type of detection, i.e., direct and indirect detection. The detection may be qualitative or quantitative detection or measurement. In some embodiments, the method of the present invention comprises detecting a marker (biomarker) or chemokine. In some embodiments, the detection is measuring an amount or level (e.g., mRNA expression level) of the marker or chemokine, or measuring an average and/or a total of such levels.

Herein, "marker" (also called "biomarker") refers to an indicator for prediction, diagnosis, prognosis, or the like, which can be detected or measured in a sample from a patient. The marker may serve as an indicator of cancer with certain pathological or clinical features, for example, a cancer which is responsive to a therapy comprising administration of an effective amount of a PD-1/PD-L1 inhibitor such as an anti-PD-1 antibody or anti-PD-L1 antibody. Markers include, but are not limited to, polynucleotides (mRNA, DNA, etc.), polypeptides, polypeptide and polynucleotide modifications (e.g. posttranslational modifications), carbohydrates, etc. In some embodiments, a marker is an mRNA or transcript of a gene. In the present invention, such markers include dendritic cell markers and chemokines.

In some embodiments, the presence and/or expression level/amount of a marker(s) in a sample may be measured or evaluated by known methods understood by those skilled in the art. The methods include, but are not limited to: RNA-Seq (a state-of-the-art RNA sequencing technique that can also detect or quantify RNA expression levels), Northern analysis, polymerase chain reaction (PCR) such as quantitative real time PCR (qRT-PCR) and other methods such as branched DNA, NASBA (nucleic acid-based amplification), TMA (transcription-mediated amplification) and the like, FISH, microarray analysis, gene expression profiling, serial analysis of gene expression (SAGE), immunohistochemistry (IHC), Western blotting, immunoprecipitation, ELISA, ELIFA, flow cytometry (FCM) (also called fluorescence activated cell sorting (FACS)), MassARRAY, proteomics, quantitative blood assays such as Serum ELISA, in situ hybridization, and any other assays performed on RNA, protein, gene, and any tissue array methods. Protocols for evaluating gene expression can be found, e.g., Ausubel et al., eds., 1995, Current Protocols In Molecular Biology.

In some embodiments, the marker is detected or measured (e.g., quantified) in a sample by mRNA expression of the marker. In some embodiments, mRNA expression is detected or measured by RNA-seq, qPCR, rtPCR, multiplex qPCR or RT-qPCR, microarray analysis, nano string, SAGE, MassARRAY, FISH, etc.

The "expression level", "level", "amount", or "quantity" of a marker associated with the pathological or clinical features is a detectable level/quantity in a sample from a patient. It can be measured by methods known in the art or those described herein. The expression level of a marker can be used to predict the patient's response to a cancer therapy.

Herein, "expression level" refers to the amount of a marker in a sample from a patient. The term "expression" refers to the conversion of genetic information into molecular structures in the cell. Thus, "expression" includes transcription into an mRNA, translation into a polypeptide/protein, polynucleotide modifications, polypeptide modifications, etc. Transcripts generated by alternative splicing, degraded transcripts, and polypeptides after post-translational processing may be included in "expressed" molecules.

In some embodiments, an increased expression of a marker(s) related to development of DCs and/or a chemokine indicates that the patient is more likely to receive higher clinical benefit when the patient is treated by the therapy using a PD-1/PD-L1 inhibitor such as an anti-PD-1 antibody or anti-PD-L1 antibody. In some embodiments, the clinical benefit includes a relative increase in, e.g., overall survival (OS), progression free survival (PFS), complete response (CR), partial response (PR), etc.

Herein, "sample" refers to a substance obtained or derived from a patient or subject containing cellular molecules to be detected or measured, e.g., based on their amount, quantity, physical, biochemical, chemical and/or physiological characteristics. Herein, "tumor sample" or "cancer sample" refers to any sample obtained from the tumor or cancer of a patient to be characterized. Without any limitations, samples include: cells (primary or cultured), cell supernatants, cell lysates, amniotic fluid, blood-derived cells, cerebrospinal fluid, follicular fluid lymph fluid, plasma, milk, mucus, perspiration, platelets, saliva, seminal fluid, serum, sputum, synovial fluid, tears, tissue culture medium, tissue extracts, tissue homogenates, tumor cells, tumor cell extracts, tumor tissues, tumor lysates, urine, vitreous fluid, and whole blood.

In some embodiments, the sample is a tissue sample or tumor tissue sample from a patient. In some embodiments, the tissue sample may comprise tumor cells, tumor-infiltrating immune cells, stromal cells, etc. In some embodiments, the sample is a clinical sample. In some embodiments, the sample is used for identifying or selecting a patient. In some embodiments, the sample is obtained from a tumor which is primary or metastatic in a patient. To obtain a tissue sample, biopsy may be used to collect a representative piece of a tumor tissue.

Herein, "tissue sample" or "cell sample" refers to tissues or cells collected from a patient/subject to be tested. Herein, "tumor tissue sample" or "tumor cell sample" refers to tumor tissues or cells collected from the cancer or tumor of a patient/subject. The tissue/cell sample may be obtained from solid tissue from a fresh or frozen/preserved organ, biopsy, blood, blood components, plasma, amniotic fluid, cerebral spinal fluid, interstitial fluid, peritoneal fluid, cells from the patient/subject. The tissue/cell sample may contain primary or cultured cells. The tissue sample may contain additional, non-natural components including antibiotics, anticoagulants, buffers, fixatives, nutrients, preservatives, etc.

In some embodiments, the sample is a tissue sample or tumor tissue sample, e.g., biopsy tissue, obtained from a patient. In some embodiments, the tissue sample is obtained from any the following tissues/cells: bladder tissue; breast tissue; colorectal tissue; esophageal tissue; gastric tissue; head and neck tissue; lung tissue; mesothelial tissue; osteosarcoma tissue; ovarian tissue; pancreatic tissue; prostate tissue; renal tissue; skin tissue; thyroid tissue; urothelial tissue; blood cells; bone; bone marrow; liver tissue; lymph nodes, etc. In some embodiments, the sample is a lung tissue sample.

Herein, "response" (or variations thereof such as "responsive" and "responsiveness") refers to a patient' response that is evaluated by any endpoint showing or suggesting a benefit to the patient. They include, but not limited to, inhibition of cancer/tumor progression such as complete arrest, slowdown, etc.; reduction in the cancer/tumor size; inhibition, reduction, complete stop, or slowdown of infiltration into peripheral organs/tissues; inhibition, reduction, complete stop, or slowdown of metastasis; relief of a symptom(s) associated with the cancer/tumor; increase in the length of survival (e.g., overall survival and progression free survival); and reduced mortality at a certain time point after cancer therapy or treatment.

In the evaluation of the response or responsiveness of tumor/cancer to the treatment/therapy, the Best Overall Response (BOR) is defined as the best response recorded from the start of the treatment until the cancer progression/recurrence. For the response, the following criteria can be used: Complete Response (CR); Partial Response (PR); Stable Disease (SD); and Progressive Disease (PD). Their definitions are known to those skilled in the art.

Herein, "responsiveness" (or grammatical variations thereof such as "(being) responsive (to)") of a patient to therapy using a medicament (e.g., anti-PD-L1 antibody) refers to clinical or therapeutic benefits for the patient suffering from or suspected of suffering from a disease such as cancer or tumor. The benefits include, but are not limited to the following: (i) extension or prolongation of survival (e.g., overall survival (OS) and progression free survival (PFS)); (ii) a response of interest (e.g., complete response (CR), partial response (PR), stable disease (SD), disease control rate (DCR; CR+PR+SD), etc.); or (iii) improving signs or ameliorated symptoms of cancer/tumor. The presence or elevation of expression of a marker may be used to identify a patient who is more likely to respond to the therapy, relative to a patient that does not have the presence or elevation of expression of the marker. The presence or elevation of expression of the marker may be used to predict or determine that the patient can/will have an increased likelihood of benefit from the therapy, relative to a patient that does not have the presence or elevation of expression of the marker.

Herein, "therapy" (e.g., "anti-cancer/tumor therapy") refers to a medical intervention useful for treating a disease (e.g., cancer/tumor). Medicaments or anti-cancer therapeutic agents can be used in the therapy. They include, but are not limited to, inhibitors such as PD-1/PD-L1 inhibitors including PD-1 inhibitors and PD-L1 inhibitors which inhibit binding between PD-1 and PD-L1, antibody pharmaceuticals such as anti-PD-1 antibodies and anti-PD-L1 antibodies, agents used in radiation therapy, antiangiogenesis agents, anti-tubulin agents, apoptotic agents, chemotherapeutic agents, cytotoxic agents, growth inhibitory agents, and any other agents or pharmaceuticals to treat cancer/tumor, platelet derived growth factor inhibitors, COX-2 inhibitors, interferons, cytokines, antagonists/agonists that bind to cancer-related molecules, etc.

"Chemokines (chemoattractants)" are known to be involved in the maintenance of lymphatic tissues and the control of inflammation through cell migration, differentiation, and activation. They also have been reported to play critical roles in recruiting immune cells in tumor tissues as well as lymph nodes. Chemokines are proteins of about 70 to 100 amino acid residues, and classified into four subfamilies, CC, CXC, CX3C, and C, according to the amino acid sequence motif with cysteine residues. As for chemokines belonging to the C subfamily, mouse XCL1 and human XCL1 and XCL2 are known. XCR1 (also called GPR5) is a receptor for XCL1 and XCL2, i.e., XCL1 and XCL2 function as agonists of XCR1 (which is a dendritic cell marker described herein). Mouse XCR1 is mainly expressed on CD8+/CD103+ dendritic cells (DCs) in lymphoid tissues and peripheral tissues. Human XCR1 is expressed on CD141+ dendritic cells (DCs) which are similar to the mouse dendritic cells (DCs).

Mouse XCR1+/CD8+/CD103+ dendritic cells (DCs) and human XCR1+/CD141+ dendritic cells (DCs) have strong cross-presentation ability. In "normal" antigen presentation, only proteins synthesized by the cell itself are degraded by proteasome and loaded on major histocompatibility complex (MHC) class I and presented to CD8+ T cells, and products taken up from outside the cell by phagocytosis and degraded by endosomes and lysosomes are loaded on MHC class II and presented to CD4+ T cells. In contrast, in cross-presentation, endosomal and lysosomal degraded products are loaded on MHC class I and presented to CD8+ T cells to induce differentiation and proliferation to cytotoxic T cells. Cross-presentation is thought to be important for cytotoxic activity against tumors. Herein, "cross-presentation ability" or "cross-presenting ability" refers to the ability of dendritic cells (DCs) to present the product to T cells. Herein, dendritic cells (DCs) having this ability may be referred to as "cross-presentation (cross-presenting) dendritic cells (DCs)". In the case of CD8-positive T cells, the ability is referred to as "cross-presentation ability to CD8-positive T cells" or "cross-presenting ability to CD8-positive T cells".

An important function of chemokine is to accumulate effector T cells in tumor. Examples of chemokines include CXCL9 (also called MIG; UniProtKB: Q07325 (human); for example, the nucleotide and amino acid sequences are shown in SEQ ID NOs: 2 and 10, respectively), CXCL10 (also called IP-10; UniProtKB: P02778 (human); for example, the nucleotide and amino acid sequences are shown in SEQ ID NOs: 3 and 11, respectively), and CXCL11 (also called I-TAC; UniProtKB: 014625 (human); for example, the nucleotide and amino acid sequences are shown in SEQ ID NOs: 4 and 12, respectively). In summary, CXCL9, 10, and 11 belong to the CXC chemokine family and function as ligands for CXCR3. They are produced by cells such as macrophages, dendritic cells (DCs) and fibrocytes stimulated with inflammatory cytokines, especially interferon-gamma. CXCR3 is a chemokine receptor that is highly expressed on effector T cells and plays a critical role in T cell trafficking. CXCR3 expression is induced by activation of naive T cells. Specifically, CXCL9 interacts with CD8+ T cells to play an important role in lymphocyte trafficking. CXCL10 is secreted from fibroblasts and macrophages etc. stimulated with inflammatory cytokines and has chemotactic activity on monocytes, macrophages, T cells, and NK cells. CXCL11 is a low-molecular-weight chemokine which attracts activated T cells, monocytes, B cells, Th1 lymphocytes, and NK cells.

Dendritic cell markers may be used in the present invention. An intratumoral amount/quantity/number of dendritic cells (DCs) in a tumor tissue sample obtained from a patient with cancer (e.g., tumor-infiltrating DCs or functional DCs with cross-presenting ability (cross-presentation ability) can be indicative of response to PD-1/PD-L1 inhibitors such as anti-PD-1 antibodies and anti-PD-L1 antibodies. Thus, in some embodiments, the markers of the present invention may be markers for estimating an intratumoral amount of DCs. The intratumoral amount of DCs may be estimated or determined by detecting the levels of expression of markers associated with activation, development, and/or maturation of DCs with cross-presenting ability. The markers include, but are not limited to, XCR1, Clec9, Irf8, and Batf3. The markers may be used separately as individual markers, or in combination of two or more markers as a cumulative expression of the markers, e.g., cumulative DC gene score (DC score). The expressions of multiple markers can be combined by any appropriate mathematical method known in the art to obtain a DC score. DC scores may be obtained based on the expression levels of the markers described herein.

In some embodiments, the present invention provides:

a method of identifying a patient who has or is suspected of having a cancer which is responsive to a therapy comprising administration of an effective amount of a PD-1/PD-L1 inhibitor (which may be a PD-1 inhibitor or PD-L1 inhibitor that can inhibit binding between PD-1 and PD-L1, such as an anti-PD-1 antibody or anti-PD-L1 antibody; the same applies to other embodiments disclosed herein), wherein the method comprises:

detecting (i) and (ii) below in a sample from the patient:

(i) at least one marker which is an antigen-presenting cell marker or an antigen presentation marker; and (ii) at least one chemokine or chemoattractant.

In some embodiments, the present invention provides:

a method of identifying a patient who has or is suspected of having a cancer which is responsive to a therapy comprising administration of an effective amount of a PD-1/PD-L1 inhibitor, wherein the method comprises:

detecting (i) and (ii) below in a sample from the patient:

(i) at least one marker for estimating an intratumoral amount of dendritic cells (DCs) having cross-presentation ability to CD8-positive T cells; and (ii) at least one chemokine that accumulates effector T cells in tumor.

Throughout the specification/claims, "(a method of) identifying a patient" may be rephrased as "(a method of) selecting a patient", "(a method of) screening a patient", "(a method of) screening for patients", etc.

In some embodiments, the antigen-presenting cell marker (or antigen presentation marker) is a dendritic cell marker which is expressed on or in dendritic cells (DCs).

In some embodiments, the chemokine or chemoattractant is a T cell chemokine or T cell chemoattractant which attract T cells by being recognized or bound by a T cell chemokine receptor on the surface of T cells.

In some embodiments, the present invention provides:

a method of identifying a patient who has or is suspected of having a cancer which is responsive to a therapy comprising administration of an effective amount of a PD-1/PD-L1 inhibitor (such as an anti-PD-1 antibody or anti-PD-L1 antibody), wherein the method comprises:

detecting (i) and (ii) below in a sample from the patient:

(i) at least one marker for estimating an intratumoral amount of dendritic cells (DCs) having cross-presentation ability to CD8-positive T cells; and (ii) at least one chemokine that accumulates effector T cells in tumor.

In some embodiments, the present invention provides a method of detecting (i) and (ii) below in a sample from a human subject:

(i) at least one marker for estimating an amount of dendritic cells (DCs) having cross-presentation ability to CD8-positive T cells; and (ii) at least one chemokine that accumulates effector T cells.

In some embodiments, the present invention provides a method of predicting the therapeutic effect (or efficacy) of a PD-1/PD-L1 inhibitor (such as an anti-PD-1 antibody or anti-PD-L1 antibody) on a cancer patient, wherein the method comprises: detecting (i) and (ii) below in a sample from the patient:

(i) at least one marker for estimating an intratumoral amount of dendritic cells (DCs) having cross-presentation ability to CD8-positive T cells; and (ii) at least one chemokine that accumulates effector T cells in tumor.

In some embodiments, the therapy comprises administration of an effective amount of a PD-1/PD-L1 inhibitor. In some embodiments, the PD-1/PD-L1 inhibitor is an anti-PD-1/PD-L1 antibody. In some embodiments, the anti-PD-1/PD-L1 antibody is a humanized anti-PD-1/PD-L1 antibody. In some embodiments, the humanized anti-PD-1/PD-L1 antibody is atezolizumab. Preferably, the therapy is conducted on a patient who has or is suspected of having a cancer which is responsive to the therapy.

The terms "cancer" and "cancerous" refer to or describe the physiological condition in mammals that is typically characterized by unregulated cell growth/proliferation. Examples of cancer include, but are not limited to: carcinoma, lymphoma (e.g., Hodgkin's and non-Hodgkin's lymphoma), blastoma, sarcoma, melanoma, and leukemia such as acute lymphoblastic leukemia. More particular examples of such cancers include squamous cell cancer, lung cancer, small cell lung cancer (SCLC), non-small cell lung cancer (NSCLC), adenocarcinoma of the lung, squamous carcinoma of the lung, cancer of the peritoneum, hepatocellular cancer, gastric cancer, gastrointestinal cancer, pancreatic cancer, glioma, cervical cancer, ovarian cancer, liver cancer, bladder cancer, urothelial carcinoma, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma, leukemia and other lymphoproliferative disorders, and various types of head and neck cancer. In some embodiments, the cancer is a cancer to which an anti-PD-1 or anti-PD-L1 antibody is applicable. In some embodiments, the cancer is a cancer to which atezolizumab is applicable. Whether it is applicable to the cancer (or whether the cancer is treatable with it) can be appropriately understood by a skilled person or medical practitioner in view of the drug approval received from the authority such as the Food and Drug Administration (FDA) of the United States, or the knowledge in the art. In some embodiments, the cancer is selected from the group consisting of: breast cancer, non-small cell lung cancer, small cell lung cancer, and bladder cancer such as urothelial carcinoma, and alveolar soft part sarcoma. In some embodiments, the cancer is non-small cell lung cancer.

The term "tumor" refers to all neoplastic cell growth and proliferation, whether malignant or benign, and all pre-cancerous and cancerous cells and tissues. The terms "cancer", "cancerous", and "tumor" are not mutually exclusive as referred to herein.

Herein, a patient who "is suspected of having a cancer" refers to a patient who is likely to have or possibly/probably has a cancer in consideration of subjective symptoms, objective symptoms, and results of predictive cancer diagnosis such as: imaging analysis using, e.g., X-rays, computed tomography (CT), magnetic resonance imaging (MRI), positron emission tomography (PET), and single-photon emission computed tomography (SPECT); analysis of body fluid such as blood and urine; analysis of patient-derived nucleic acids such as DNA and RNA; and any predictive analysis for diagnosing the cancer.

In some embodiments, the marker is a non-T cell activation marker, i.e., the marker is not a T cell activation marker. If such a T cell activation marker is used as the marker for the prediction, there is a concern that one can fail to identify potential patients who are expected to be responsive to a PD-1/PD-L1 inhibitor, in which PD-1 or PD-L1 has been expressed at a low level or has not been expressed, the IFN-gamma pathway has not been activated, or little activated T cells have infiltrated into tumor, but the activation has been prepared in draining lymph nodes. In addition, there is also a concern that patients without the cancer antigen in whom a PD-1/PD-L1 inhibitor is ineffective may also be selected by including all patients in whom PD-L1 is constitutively expressed in tumor. Thus, preferably, the present invention may exclude the use of such a T cell activation marker. T cell activation markers are known in the art and include, but are not limited to, CD69, CD25, CD28, CD38, CD40L, IFN-gamma, PD-1, CD8, granzymes, and perforin.

In some embodiments, the marker is an antigen-presenting cell (APC) marker or antigen presentation marker. In some embodiments, the marker is a dendric cell marker. In some embodiments, the marker is a cross-presenting (cross-presentation) dendritic cell marker. In some embodiments, the marker is one or more markers selected from the group consisting of: XCR1, Clec9, Irf8, Batf3, CD205, CD103, and CD141, which are specific examples of dendritic cell markers, in particular, cross-presenting dendritic cell markers. In some embodiments, the marker is one or more markers selected from the group consisting of: XCR1, Clec9, Irf8, and Batf3. In some embodiments, the marker(s) is/are one, two, three, or all of: XCR1, Clec9, Irf8, and Batf3. In some embodiments, the marker is XCR1 alone.

In some embodiments, the chemokine is a T cell chemoattractant. In some embodiment, the chemokine is a chemokine that accumulates effector T cells in tumor. In some embodiments, the chemokine is a CXCR3 ligand. In some embodiments, two, three, or more CXCR3 ligands are used in combination as the chemokines. In some embodiments, the chemokine(s) is/are one, two, or all of: CXCL9, CXCL10, and CXCL11. In some embodiments, the chemokines are all of: CXCL9, CXCL10, and CXCL11.

Herein, "patient group" refers to a population of patients who suffers from or is suspected to suffer from the same type of disease, and (will) undergo the same type of medical treatment. In some embodiments, the patient in the present invention belongs to a patient group. Such a patient group can be suitably determined, and may have any size. In some embodiments, a patient group consists of patients who have or are suspected of having a cancer. In some embodiments, a patient group consists of patients having various levels of intratumoral PD-L1 expressions which may be low or high. In some embodiments, a patient belongs to a patient group comprising patients having a low (lower) intratumoral PD-L1 expression, as well as patients having a high (higher) intratumoral PD-L1 expression. The present invention enables identification of potential patients who are expected to be responsive to the therapy and has low or no PD-L1 expression, in addition to patients who are expected to be responsive to the therapy and has relatively high PD-L1 expression. The present invention can detect the whole effective group of patients for the PD-1/PD-L1 inhibitor (e.g., anti-PD-1 antibody or anti-PD-L1 antibody) including patients who has relatively low or no PD-L1 expression in tumor. The threshold value defining the "high/low" expression is discussed elsewhere herein.

In some embodiments, the methods of the present invention detects: (i) at least one marker; and (ii) at least one chemokine. In some embodiments, the methods of the present invention detects: (i) at least one marker; and (ii) one, two, three, or more chemokines. In some embodiments, the detecting of (i) is measuring a mRNA expression level of the marker, and the detecting of (ii) is measuring a mRNA expression level(s) of one, two, three, or more chemokines. In some embodiments, the detecting of (i) and (ii) is measuring an average ("AP/T score") of mRNA expression levels of the marker and one, two, three, or more chemokines. In the present invention, chemokines may be used in combination as biomarkers including chemokines that accumulate effector T cells, such as CXCL9, CXCL10, and CXCL11. In some embodiments, the marker is XCR1, and the chemokine(s) is/are one, two, or three (all) of CXCL9, CXCL10, and CXCL11. Compared to the use of a single marker, the combination of the biomarkers is expected to enhance the accuracy of the predictive analysis.

In some embodiments, the method further comprises determining whether the marker and the chemokine are detected. In some embodiments, the method further comprises determining whether the mRNA expression levels (or an average expression level; "AP/T score") of the marker and the chemokine(s) are equal to or more than a threshold value.

In some embodiments, the method further comprises identifying the patient as a patient (subject) on whom the therapy is conducted, if the mRNA expression levels (or an average expression level; "AP/T score") of the marker and/or the chemokine(s) are equal to or more than a threshold value. In some embodiments, the method further comprises determining that the therapy is conducted on the patient/subject, if the mRNA expression levels (or an average expression level; "AP/T score") of the marker and/or the chemokine(s) are equal to or more than a threshold value. In some embodiments, the method further comprises conducting the therapy on the (identified) patient/subject. In some embodiments, the method further comprises administering an effective amount of a PD-1/PD-L1 inhibitor such as an anti-PD-1 antibody or anti-PD-L1 antibody, to the patient/subject.

In some embodiments, in the method of the present invention, the detection (e.g., detecting of (i) and (ii) mentioned herein) is determining an average ("AP/T score") of (a) and (b) below: (a) a mRNA expression level of the marker; and (b) a mRNA expression level(s) of the chemokine(s). In some embodiments, wherein the detection is determining an average ("AP/T score") of (a) and (b) below: (a) a mRNA expression level of the marker; and (b) a mRNA expression level(s) of one, two, three, or more chemokines. In some embodiments, the marker is XCR1, and the chemokines are selected from CXCL9, CXCL10, and CXCL11. In some embodiments, the marker is XCR1, and the chemokines are all of CXCL9, CXCL10, and CXCL11. In some embodiments, the method further comprises determining whether the average ("AP/T score") is equal to or more than a threshold value.

In some embodiments, the method further comprises identifying the patient as a patient/subject on whom the therapy is conducted, if the average ("AP/T score") is equal to or more than the threshold value. In some embodiments, the method further comprises determining that the therapy is conducted on the patient/subject if the average ("AP/T score") is equal to or more than the threshold value. In some embodiments, the method further comprises conducting the therapy on the (identified) patient/subject in whom the average ("AP/T score") is equal to or more than the threshold value. In some embodiments, the method further comprises administering an effective amount of the PD-1/PD-L1 inhibitor, such as an anti-PD-1 antibody or anti-PD-L1 antibody, to the patient/subject in whom the total is equal to or more than the threshold value.

In some embodiments, the method further comprises showing or predicting that the therapeutic effect (or efficacy) of a PD-1/PD-L1 inhibitor (such as an anti-PD-1 antibody or anti-PD-L1 antibody) on the patient is high (or higher), if the average ("AP/T score") is equal to or more than the threshold value (compared to when the average ("AP/T score") is less than the threshold value). In some embodiments, the degree (high/low) of the therapeutic effect (or efficacy) of the inhibitor is evaluated by a therapeutic indicator known in the art, e.g., overall survival (OS), progression free survival (PFS), complete response (CR), partial response (PR), stable disease (SD), disease control rate (DCR; CR+PR+SD), etc. In some embodiments, "high" therapeutic effect (or efficacy) means that the cancer of a patient is responsive to a therapy comprising administration of an effective amount of a PD-1/PD-L1 inhibitor such as anti-PD-1 antibody or anti-PD-L1 antibody.

In some embodiments, the present invention provides a method of treating, in a patient, a cancer which is responsive to a therapy comprising administration of an effective amount of a PD-1/PD-L1 inhibitor (such as an anti-PD-1 antibody or anti-PD-L1 antibody), wherein the method comprises:

- obtaining a tissue sample from a human having or suspected of having cancer; detecting (i) and (ii) below in a sample from the patient:
- (i) at least one marker for estimating an intratumoral amount of dendritic cells (DCs) having cross-presentation ability to CD8-positive T cells; and
- (ii) at least one chemokine that accumulates effector T cells in tumor;
- identifying a patient who has or is suspected of having a cancer which is responsive to the therapy;
- determining that the therapy is conducted on the the (identified) patient; and conducting the therapy on the (identified) patient, or administering an effective amount of the inhibitor to the patient.

Herein, "conducting the therapy" means conducting surgical therapies and/or medical treatments.

The accuracy of predicting the efficacy or effect of the method of the present invention may be assessed using a Receiver Operating Characteristic (ROC) curve which is generally used for evaluating the predictability by a predictive algorithm. The ROC curve is a plot showing the diagnostic ability of a binary classifier system with a varied threshold for discrimination. When an ROC curve is produced, an area under the (ROC) curve (AUC) is calculated. AUC varies between 0 and 1. An AUC of 0.5 means "by chance" with no predictability. Generally, the following categorization is made: an AUC of 0.5 to 0.7, "low" accuracy; an AUC of 0.7 to 0.9, "moderate" accuracy; and an AUC of 0.9 to 1.0, "high" accuracy. An AUC of 1 means perfect performance, i.e., a sensitivity of 100% and a specificity of 100%. In the context of the present invention, for example, AUC=1 means that 100% of the mice predicted to be responsive to the therapy were actually all responsive, and 100% of the mice predicted to be non-responsive to the therapy were actually all non-responsive. The same applies to a human model. However, in a human clinical trial for cancer, the negative control may be a group administered with a conventional therapeutic agent such as docetaxel rather than a placebo. In this case, the ability of prediction of efficacy may be an increased ability over the predictability with docetaxel.

In some embodiments, the method of the present invention is a method of predicting the response of a patient to a PD-1/PD-L1 inhibitor (such as an anti-PD-1 antibody or anti-PD-L1 antibody). In some embodiments, the method of the present invention is a method of predicting the therapeutic effect (or efficacy) of a PD-1/PD-L1 inhibitor (such as an anti-PD-1 antibody or anti-PD-L1 antibody) on a patient. In some embodiments, the patient is a cancer patient.

The "threshold" or "threshold value" (also called "cut-off value" or "cut-off point") for discriminating or predicting the responsiveness and non-responsiveness to the therapy may be suitably determined. In some embodiments, the threshold value is a threshold value determined based on the levels of biomarkers (such as cell markers and chemokines) in a patient group/population. For example, for a given whole patient group, the expression levels (e.g., individual, total, or average expression levels ("AP/T scores"), or any combinations thereof) of biomarkers are measured for the patients, and they are classified into "high expression" and "low expression" groups depending on a given threshold value of the biomarker expression level. In some embodiments, the threshold value is determined such that a certain percentage (e.g., 30%, 50%, 70%, etc.) of the total patients in a patient group have an expression level which is equal to or more than the threshold value. In some embodiments, the threshold value is determined such that a certain percentage (e.g., 30%, 50%, 70%, etc.) of the total patients are included in the "high expression" group with expression levels which are equal to or more than the threshold value, and the remainder (e.g., 30%, 50%, 70%, etc.) of the total patients are included in the "low expression" group with expression levels which are less than the threshold value. If the threshold value is elevated, e.g., the percentage of the "high expression" group is reduced, then patients with expectedly higher responsiveness for the therapy may be selected, whereas the sensitivity may be lowered and patients with expectedly lower responsiveness may be excluded. Thus, the threshold value may be suitably determined depending on the desired responsiveness to the therapy and the desired sensitivity to potential patients. In some embodiments, the threshold value may vary such that 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, or 70% of the total patients are included in the "high expression" group, i.e., 70%, 69%, 68%, 67%, 66%, 65%, 64%, 63%, 62%, 61%, 60%, 59%, 58%, 57%, 56%, 55%, 54%, 53%, 52%, 51%, 50%, 49%, 48%, 47%, 46%, 45%, 44%, 43%, 42%, 41%, 40%, 39%, 38%, 37%, 36%, 35%, 34%, 33%, 32%, 31%, or 30% of the total patients are included in the "low expression" group. In some embodiments, the threshold value is determined such that X % of the total patients of a patient group have an expression level which is equal to or more than the threshold value, where X=30 to 70, e.g., X equals to any one of the above-mentioned percentages. In some embodiments, the percentage of the total patients is 30%, 50%, or 70%. To specify the threshold or cut-off value, the term "percentile" may be used. For example, "xth percentile" refers to the value (or score) below which x % of the observations, i.e., data of x % of the total patients, are found, where x refers to any one of the above-mentioned percentages such as 30, 50, 70, etc.

In some embodiments, the present invention provides a method of selecting a patient who has or is suspected of having a cancer which is responsive to a therapy comprising administration of an effective amount of a PD-1/PD-L1 inhibitor (such as an anti-PD-1 antibody or anti-PD-L1 antibody), wherein the method comprises:

determining a patient group consisting of patients who have or are suspected of having a cancer;

measuring an average ("AP/T score") of (i) and (ii) below in a sample from each (and every) patient in the patient group:

(i) a mRNA expression level of a marker for estimating an intratumoral amount of dendritic cells (DCs) having cross-presentation ability to CD8-positive T cells; and (ii) a mRNA expression level(s) of one or more chemokines that accumulate effector T cells in tumor;

determining a threshold value such that a certain percentage of the total patients in the patient group have the average ("AP/T score") which is equal to or more than the threshold value; and selecting a patient with the average ("AP/T score") which is equal to or more than the threshold value.

In some embodiments, the present invention provides a method of predicting the therapeutic effect (or efficacy) of a PD-1/PD-L1 inhibitor (such as an anti-PD-1 antibody or anti-PD-L1 antibody) on a cancer patient in a patient group, wherein the method comprises:

determining a patient group consisting of patients who have or are suspected of having a cancer;

measuring an average ("AP/T score") of (i) and (ii) below in a sample from each patient in the patient group:

(i) a mRNA expression level of at least one marker for estimating an intratumoral amount of dendritic cells (DCs) having cross-presentation ability to CD8-positive T cells; and (ii) a mRNA expression level(s) of one or more chemokines that accumulate effector T cells in tumor;

determining a threshold value such that a certain percentage of the total patients in the patient group have the average ("AP/T score") which is equal to or more than the threshold value; and showing (or predicting) that the therapeutic effect (or efficacy) of the inhibitor is high on a patient with the average ("AP/T score") which is equal to or more than the threshold value.

In some embodiments, the present invention provides kits (articles of manufacture) comprising one or more reagents for determining the presence or quantity of at least one marker and/or chemokine in a sample from a patient with a cancer/tumor.

In some embodiments, the present invention provides kits (or articles of manufacture) comprising: one or more reagents for determining the presence or quantity of at least one marker and/or chemokine in a sample from a patient with a cancer/tumor; and a package insert indicating that the one or more reagents is used for identifying or selecting a patient who has or is suspected of having a cancer which is responsive to a therapy comprising administration of an effective amount of a PD-1/PD-L1 inhibitor (such as an anti-PD-1 antibody or anti-PD-L1 antibody), based on the presence or quantity of the marker/chemokine. In some embodiments, the present invention provides a method for manufacturing a kit (or an article of manufacture) comprising combining in a package: one or more reagents for determining the presence or quantity of at least marker and/or chemokine in a sample from a patient with a cancer/tumor; and a package insert indicating that the one or more reagents is used for identifying or selecting a patient who has or is suspected of having a cancer which is responsive to a therapy comprising administration of an effective amount of a PD-1/PD-L1 inhibitor (such as an anti-PD-1 antibody or anti-PD-L1 antibody), based on the presence or quantity of the marker/chemokine.

In some embodiments, the kit (or article of manufacture) comprises a container and a package insert or label (mentioned herein) on or attached to with the container. The package insert or label may have any form such as paper, electronic media such as magnetically recorded medium, CD, DVD, etc. Containers may include bottles, vials, syringes, etc. The containers may be formed of a material(s) such as glass or plastic. The kit (or article of manufacture) may also contain other materials for reaction such as buffers, diluents, filters, etc.

In some embodiments, the present invention provides use of one or more reagents for determining the presence or quantity of at least one marker and/or chemokine in a sample from a patient with a cancer/tumor, in the manufacture of a kit (or article of manufacture) for use in identifying or selecting a patient who has or is suspected of having a cancer which is responsive to a therapy comprising administration of an effective amount of a PD-1/PD-L1 inhibitor (such as an anti-PD-1 antibody or anti-PD-L1 antibody), based on the presence or quantity of the marker/chemokine.

The reagents may be those used in any of the following detection/quantification methods: RNA-Seq, Northern analysis, polymerase chain reaction (PCR) such as quantitative real time PCR (qRT-PCR) and other methods such as branched DNA, NASBA (nucleic acid-based amplification), TMA (transcription-mediated amplification) and the like, FISH, microarray analysis, gene expression profiling, serial analysis of gene expression (SAGE), immunohistochemistry (IHC), Western blotting, immunoprecipitation, ELISA, ELIFA, flow cytometry (FCM) (also called fluorescence activated cell sorting (FACS)), MassARRAY, proteomics, quantitative blood assays such as Serum ELISA, in situ hybridization, and any other assays performed on RNA, protein, gene, and any tissue array methods. In some embodiments, the reagents are those used in RNA-Seq which detect mRNA levels of one or more markers and/or chemokines.

In some embodiments, the present invention provides a kit (or article of manufacture) for identifying or selecting a patient who has or is suspected of having a cancer which is responsive to a therapy comprising administration of an effective amount of a PD-1/PD-L1 inhibitor (such as an anti-PD-1 antibody or anti-PD-L1 antibody), which comprises (i) a reagent for detecting at least one marker; and (ii) a reagent for detecting at least one chemokine. In some embodiments, the present invention provides use of (i) a reagent for detecting at least one marker; and (ii) a reagent for detecting at least one chemokine, in the manufacture of a kit (or article of manufacture) for identifying or selecting a patient who has or is suspected of having a cancer which is responsive to a therapy comprising administration of an effective amount of a PD-1/PD-L1 inhibitor (such as an anti-PD-1 antibody or anti-PD-L1 antibody). In some embodiments, the chemokine(s) is/are one, two, three, or more chemokines. In some embodiments, the detecting by the reagent of (i) is measuring a mRNA expression level of the marker, and the detecting by the reagent of (ii) is measuring mRNA expression levels of one, two, three, or more chemokines. In some embodiments, the kit (or article of manufacture) is for use in measuring an average ("AP/T score") of a mRNA expression level of the marker and a mRNA expression level(s) of one, two, three, or more chemokines. In some embodiments, the chemokines are selected from the group consisting of CXCL9, CXCL10, and CXCL11. In some embodiments, the marker is XCR1, and the chemokines are all of CXCL9, CXCL10, and CXCL11. In some embodiments, the marker is XCR1, and the chemokines are CXCL9 and CXCL10. In some embodiments, the marker is XCR1, and the chemokines are CXCL10 and CXCL11. In some embodiments, the marker is XCR1, and the chemokines are CXCL9 and CXCL11. In some embodiments, the marker is XCR1, and the chemokines is CXCL9. In some embodiments, the marker is XCR1, and the chemokines is CXCL10. In some embodiments, the marker is XCR1, and the chemokines is CXCL11. In some embodiments, the kit (or article of manufacture) is for use in determining whether the average ("AP/T score") of the mRNA expression level of the marker and the mRNA expression levels of the chemokines is equal to or more than a threshold value. The threshold value may be determined according to the disclosures herein.

Although the present invention has been or will be described herein in some detail by way of illustration and example for purposes of clarity of understanding, the descriptions and examples should not be construed as limiting the scope of the invention. The disclosures of all patent and scientific literature cited herein are expressly incorporated in their entirety by reference.

EXAMPLES

The following are examples of methods and compositions of the invention. It is understood that various other embodiments may be practiced, given the general description provided above.

Overview of the Experimental Design

The inventors tested the antitumor effect of an anti-mouse PD-L1 monoclonal antibody (mAb) in vivo in murine models. Flow cytometry, tumor-stimulated IFN gamma release assay, repertoire analysis, RNA sequencing, protein immunoassays, and immunohistochemistry were performed on isolated tumors or on tumor-draining lymph nodes (dLN). The accuracy of predictive markers was evaluated in 17 tumor models by receiver operating characteristic (ROC) curve analysis.

Materials and Methods

Cell Lines 17 different cell lines were used. All cells were suitably maintained and transfected.

Tumor Models

Cancer cells were implanted subcutaneously into the right flank of mice.

The administration of anti-PD-L1 antibody or control IgG was started when tumor volumes reached approximately 50-200 $mm^3$ (Day 1). Anti-mouse PD-L1 mAb or Rat IgG was administered intraperitoneally to the mice at a dose of 10 mg/kg three times a week. Anti-mouse CXCR3 mAb or Hamster IgG was administered intraperitoneally at a dose of 50 micro g/head twice a week. Tumor volume (V) was estimated from the equation $V=L\times W^2\times 0.5$ (L=length; W=width). The percentage of tumor growth inhibition (TGI %) was calculated as follows: TGI %=[1−(tumor volume of treatment group on final evaluation day−tumor volume of treatment group on day 1)/(tumor volume of control group at final evaluation day−tumor volume of control group on day 1)]×100.

Flow Cytometric Analysis

For analysis of tumor-infiltrating lymphocytes, tumor tissue was excised from control-treated mice and anticancer agent-treated mice, and single-cell suspensions were obtained by mincing tumors and homogenizing them by disruption and digestion with a gentle MACS Dissociator. Cells were analyzed using an LSRFortessa X-20 cell analyzer (BD Biosciences).

RNA Sequencing (RNA-Seq)

Total RNA was isolated from tumor tissues. Sequencing was performed using the Illumina HiSeq 2500 Sequencing System (100-bp paired-end sequencing). To evaluate gene expression, RNA log expression (R) was estimated from the equation: R=log (fragments per kilobase of exon per million mapped fragments (FPKM) value for target mRNA)−log (FPKM value for housekeeping gene). AP/T score (i.e., an average) was calculated as follows: AP/T score={R (XCR1)+R(CXCL9)+R(CXCL10)+R(CXCL11)}/4

Immunohistochemistry

The localization of CD8 alpha$^+$ T cells in tumor tissue was evaluated by immunohistochemical staining of CD8 alpha. The expression of PD-L1 in tumor tissue was evaluated by immunohistochemical staining of PD-L1.

Clinical Study Design and Assessments

The study design of OAK has been previously reported (Rittmeyer A, Barlesi F, Waterkamp D, Park K, Ciardiello F, von Pawel J, et al., Lancet (London, England) 2017; 389 (10066):255-65). All patients provided signed informed consent, and the study was conducted in full accordance with the Guideline for Good Clinical Practice and the Declaration of Helsinki. For transcriptional profiling of tumors with RNA-sequencing TruSeq RNA Access technology (Illumina (registered trademark)) was used. RNA-sequencing data were generated primarily from archival tissue at baseline. To analyze relationship between the tumor gene expression and clinical outcome, as one of the simplest ways, in this example, the average mRNA levels of XCR1, CXCL9, CXCL10 and CXCL11 which is referred to as "AP/T score", and ORR and overall survival were selected respectively.

Statistical Analysis

To evaluate statistical significance in mouse model experiments, data was analyzed with the Wilcoxon test. For two groups, $P<0.05$ was considered to indicate a significant difference. For multiple groups, P values were adjusted by the Holm-Bonferroni method. Construction of the receiver operating characteristic (ROC) curves was performed, and the areas under the ROC curves (AUC) were calculated to evaluate the diagnostic accuracy and to compare AUC for all tested parameters separately. For analysis of clinical data in the OAK study, treatment arms were compared for OS individually using a univariate Cox proportional hazards model without stratification in the BEPs and their subgroups. No multiplicity correction was applied to P values or to 95% CIs. All P values are two sided. $P<0.05$ was considered to indicate a significant difference. Kaplan-Meier methodology was used to estimate the median OS and to construct the survival curves. Gene expression levels between the CR/PR group, SD group, and PD group were compared with a Kruskal-Wallis test.

Example 1

Antitumor Activity of Anti-PD-L1 mAb by PD-L1 Gene Expression in Tumor Tissues The antitumor activity of PD-L1 mAb was examined in 17 murine tumor models. PD-L1 mAb showed significant antitumor activity in six of the tumor models and these six models are categorized as sensitive tumor. In the remaining 11 tumor models, PD-L1 mAb did not show significant antitumor activity and thus these are categorized as insensitive tumor (FIG. 1A).

To examine the ability of PD-L1 to classify tumors as sensitive or insensitive to PD-L1 mAb, PD-L1 mRNA expression was measured in tumor samples by RNA sequencing and analyzed the ROC curve. The range of PD-L1 mRNA expression levels in the sensitive models was wide and overlapped the range in the insensitive tumor models. The area under the ROC curve (AUC) was 0.848. Specificity and sensitivity at the best cutoff point as indicated by Youden's index were 0.818 and 0.833, respectively (FIG. 1B).

Example 2

Anti-PD-L1 mAb Exerted Antitumor Activity in a PD-L1-Negative and Immune Desert-Like Tumor Model To examine why intratumoral PD-L1 mRNA expression did not entirely predict the antitumor activity of PD-L1 mAb in the mouse models, the mechanism of action of PD-L1 mAb in a low-PD-L1 tumor model was analyzed. As a low-PD-L1 tumor model, the FM3A model was selected, which showed the lowest intratumoral PD-L1 mRNA expression among the models classified as being sensitive to anti-PD-L1 mAb (FIG. 1B).

First, the FM3A tumors were characterized histochemically. PD-L1 immunohistochemical staining showed that nearly all of the cells in the tumor tissue were negative under conditions in which Colon 38, another sensitive tumor, showed partial positive staining (FIG. 2A). CD8 alpha immunohistochemical staining showed that CD8 alpha$^+$ T cells infiltrated into Colon 38 tumors but there were very few CD8 alpha$^+$ T cells in FM3A tumors (FIG. 2B).

Next, using flow cytometric analysis, it was found that F4/80$^+$ cells in FM3A tumors expressed PD-L1 but were found in only small numbers in the tumor tissue (FIGS. 2C and 2D). Tumor cells (CD45$^-$ cells), which expressed almost no PD-L1, constituted most of the tumor tissue (FIGS. 2C and 2D). These results show that FM3A tumors have a PD-L1-negative and immune desert-like phenotype.

Example 3

Anti-PD-L1 mAb Enhanced T Cell Priming that had Already Occurred in Lymph Nodes Then, it was investigated whether the anti-tumor activity of PD-L1 mAb in the FM3A tumor model is dependent on T cells. CD8 alpha or CD4 depletion abolished the antitumor activity of PD-L1 mAb (FIG. 3A). PD-L1 mAb significantly increased the population of T cells including CD8 alpha$^+$ cells, Foxp3-CD4$^+$ cells, and Foxp3$^+$ CD4$^+$ cells in the tumors (FIGS. 3B and 3C). To examine the levels of T cell diversity in tumors treated with PD-L1 mAb, the diversity of TCR repertoires was evaluated using Simpson's diversity index. The variation of TCR alpha in PD-L1 mAb-treated tumors was smaller than that in control tumors, and specific elements of the TCR alpha repertoire increased in PD-L1 mAb-treated tumors (FIG. 3D). Simpson's diversity index was found to be significantly lower in the PD-L1 mAb treatment group compared to the control group (FIG. 3D).

These results suggested that tumor-reactive T cells were enriched by PD-L1 mAb treatment. Thus, tumor-draining lymph nodes and the role of PD-L1 in T cell priming were focused on. First, PD-L1 expression on antigen-presenting DCs in lymph nodes was investigated. CD103$^+$CD11c$^+$ cells expressed PD-L1 in lymph nodes (FIG. 4A, left).

Next, the expression of PD-L1 receptors (PD-1 and B7-1) on CD8$^+$ T cells in lymph nodes was analyzed. Most CD8 alpha$^+$ T cells were CD44-CD62L$^+$ naive T cells which were PD-1- and B7-1-negative, but some of the CD44$^+$CD62L-CD8 alpha$^+$ effecter T cells were PD-1- and/or B7-1-positive cells (FIG. 4A, right). PD-L1 mAb increased the number of B7-1$^+$CD8 alpha$^+$ T cells, PD-1$^+$CD8 alpha$^+$ T cells, and B7-1$^+$PD-1$^+$CD8 alpha$^+$ T cells, and increased the CD69$^+$ rate of B7-1$^+$CD8 alpha$^+$ T cells, PD-1$^+$CD8 alpha$^+$ T cells, and B7-1-PD-1-CD8 alpha$^+$ T cells (FIG. 4B). The CD69$^+$ rate of B7-1$^+$PD-1$^+$CD8 alpha$^+$ T cells in the control group could not be detected because of the low number of cells (FIG. 4B).

Next, the tumor-specific T cell responses during PD-L1 mAb treatment were investigated. Using lymphocytes from tumor-draining lymph nodes, it was found that IFN gamma production was significantly increased in the control group when stimulated with FM3A cells compared to that when stimulated by MBT2 cells (MHC-matched negative control cells), and it was further significantly increased in the PD-L1 mAb group compared to that in the control group (FIG. 4C). These results suggest that tumor antigen presentation and T cell priming had already occurred in lymph nodes at baseline prior to PD-L1 mAb treatment in the FM3A model but that PD-L1 on antigen-presenting cells prevented T cell priming, and PD-L1 mAb unleashed the T cells (FIG. 6D).

Example 4

Anti-PD-L1 mAb Increased CXCR3$^+$ Activated T Cells in Lymph Nodes, Resulting in Trafficking of T Cells to Tumors Via Responding to CXCR3 Ligands Already Expressed in Tumors Next, the time course of CD8$^+$ T cell activation by PD-L1 mAb treatment in lymph nodes and tumors in the FM3A model was analyzed. PD-L1 mAb treatment increased the number of CD69$^+$CD8 alpha$^+$ T cells in lymph nodes and the percentage of these cells in tumors on Day 8 (FIG. 5A). Importantly, on Day 4, PD-L1 mAb treatment had increased these cells in lymph nodes but not in tumors (FIG. 5A). Additionally, PD-L1 mAb treatment increased the number of CXCR3$^+$CD69$^+$CD8 alpha$^+$, CXCR3$^+$ Granzyme B (GzmB)$^+$CD8 alpha$^+$, and CXCR3$^+$Ki67$^+$CD8 alpha$^+$ T cells in lymph nodes (FIG. 5B). FM3A tumors expressed CXCR3 ligands, especially CXCL9, regardless of PD-L1 mAb treatment (FIG. 5C). CXCR3 mAb significantly prevented activated CD8 alpha$^+$ T cells from increasing in tumors as a result of PD-L1 mAb treatment but not in lymph nodes (FIG. 5D) and significantly attenuated tumor growth inhibition of PD-L1 mAb (FIG. 5E). In contrast, in the OV2944-HM-1 model, which was insensitive to PD-L1 mAb treatment, expression of CXCR3 ligands in the tumor was lower than that in the FM3A model, and it was confirmed that PD-L1 mAb treatment increased the number of $CD69^+CD8$ alpha$^+$ T cells in lymph nodes but not in tumors (FIG. 5F). These results indicated that the time lag between the PD-L1 mAb-induced increase in activated $CD8^+$ T cells in the lymph nodes and the increase in activated $CD8^+$ T cells in tumors was caused by T cell trafficking from lymph nodes to tumors expressing CXCR3 ligands.

Example 5

Antitumor Activity of Anti-PD-L1 mAb Predicted by Expression of Genes Related to Cross-Presentation DCs and Expression of CXCR3 Ligands in Tumor Tissues Two biological characteristics of the FM3A model would explain the anti-tumor activity of PD-L1 mAb treatment via enhancing T cell priming in lymph nodes and accelerating T cell trafficking to tumors: (i) tumor antigen presentation to T cells in the draining lymph nodes and (ii) expression of CXCR3 ligands in tumors.

For tumor antigen presentation to T cells in the draining lymph nodes, a series of stepwise events must be initiated (Chen D S, Mellman I., Immunity 2013; 39(1):1-10). In the first step, tumor antigens are captured in tumors by antigen cross-presenting cells (APCs) for processing. XCR1 (Yamazaki C, et al., Journal of immunology (Baltimore, Md.: 1950) 2013; 190(12):6071-82; UniProtKB: P46094 (human); for example, the nucleotide and amino acid sequences are shown in SEQ ID NOs: 5 and 13, respectively), Clec9a (Piva L, et al., Journal of immunology (Baltimore, Md.: 1950) 2012; 189(3):1128-32; UniProtKB: Q6UXN8 (human); for example, the nucleotide and amino acid sequences are shown in SEQ ID NOs: 6 and 14, respectively), Irf8 (Tailor P, et al., Blood 2008; 111(4):1942-5; UniProtKB: Q02556 (human); for example, the nucleotide and amino acid sequences are shown in SEQ ID NOs: 7 and 15, respectively), and Batf3 (Hildner K, et al., Science (New York, NY) 2008; 322(5904):1097-100; UniProtKB: Q9NR55 (human); for example, the nucleotide and amino acid sequences are shown in SEQ ID NOs: 8 and 16, respectively) are known as markers of APCs. To examine the ability of these APC markers to classify tumors as PD-L1 mAb-sensitive or -insensitive, the mRNA of these in tumors was measured, and they were analyzed by ROC curve. The AUC values of XCR1, Clec9a, Irf8, and Batf3 were 0.894, 0.621, 0.742, and 0.515, respectively (FIG. 6A). The specificity/sensitivity of these were 0.818/0.833, 0.727/0.667, 0.818/0.667, and 0.818/0.333 respectively.

Next, to examine the relation between the antitumor activity of PD-L1 mAb and expression of CXCR3 ligands, the mRNA expressions of CXCL9, CXCL10, and CXCL11 were measured, and the ROC curves were analyzed. The AUC values of each of the three CXCR3 ligands as a single factor were 0.939, 0.879, and 0.833, respectively, and the AUC value obtained by using the average of the three was 0.970 (FIG. 6B). The specificity/sensitivity of the three CXCR3 ligands were 1.000/0.833, 0.818/0.833, and 0.909/0.833, respectively, and the specificity/sensitivity obtained by using the average of the three was 0.909/1.000. Thus, the AUC, sensitivity, and specificity of any one factor was still less than perfect.

It was considered that sensitive tumors would have both characteristic (i) tumor antigen presentation in the draining lymph nodes and characteristic (ii) expression of CXCR3 ligands in tumors at baseline. Thus, the inventors created a combined biomarker—the Antigen-Presentation-related gene expression and T cells-attracting-related gene expression combined biomarker (AP/T score)-defined as the averaged expression of XCR1 and the CXCR3 ligands was conducted. The AUC, sensitivity, and specificity of the AP/T score reached each 1.000 (FIG. 6C).

Example 6

Predictability of the AP/T Score, a Combined Gene Expression Levels of XCR1 and CXCR Ligands Defined Above, was Assessed Using OAK Clinical Phase 3 Study Data Retrospectively Having demonstrated that a combination of XCR1 and CXCR3 ligands expression was associated with efficacy in the preclinical models, this AP/T score, the average expression of XCR1, CXCL9, CXCL10 and CXCL11, was also tested for its usefulness by applying this to patient's tissue gene expression data obtained in the OAK study, a clinical phase 3 trial. The AP/T scores were higher in only atezolizumab-treated patients who achieved CP/PR (FIG. 7A), with no such trend seen in the docetaxel arm. Of further importance, improved OS benefit was observed for all of three score cut-off points (above or equal to 30th, above or equal to 50th and above or equal to 70th percentile) relative to the biomarker-evaluable population (BEP) in the OAK study (FIG. 7B). In the subgroup with AP/T score above or equal to 50th percentile cut-off point, the OS hazard ratio (HR) was 0.76 (95% CI: 0.59-0.97); P=0.031) numerically lower than that of the BEP and the median OS was 15.0 and 11.1 months in the atezolizumab or docetaxel treatment arm, respectively. Patients with high AP/T scores (above or equal to 50th percentile) obtained significant OS benefit from atezolizumab versus docetaxel but no significant difference was observed in patients with low AP/T scores (<50th percentile). Estimated median OSs of HIGH and LOW AP/T subgroups (cut at 50th percentile) in atezolizumab arm were 15.0 and 11.8, while those in docetaxel arm were 11.1 and 9.8, respectively (FIG. 7C, 7D).

INDUSTRIAL APPLICABILITY

It was shown that an anti-PD-L1 mAb exerted antitumor activity through the blocking of PD-L1 in the dLN as well as the tumor site, which would provide a rationale to the efficacy of PD-L1 antibody in patients with little PD-L1 expression. Furthermore, it was demonstrated that a novel biomarker combining tumor antigen-presentation-related gene expression and activated T cell trafficking-related gene expression predicts the response to atezolizumab. These data indicate that this novel approach, focusing on activities in the dLN, would provide a better predictive biomarker for anti-PD-1 antibodies or anti-PD-L1 antibodies such as atezolizumab, or further extending to immune checkpoint inhibitors, than conventional biomarkers focusing on activities in the tumor site alone.

The invention claimed is:

1. A method of treating a patient who has a cancer, the method comprising:

(i) assaying, or having assayed, an mRNA expression level of XCRI in a sample from the patient comprising tumor cells or cells of a tumor-draining lymph node;

(ii) assaying, or having assayed, an mRNA expression level of each of CXCL9, CXCL10, and CXCL11 in a sample from the patient comprising tumor cells;

(iii) based on an average of the mRNA expression levels of XCR1, CXCL9, CXCL10, and CXCL11 as assayed in (i) and (ii), determining that the patient's cancer is likely responsive to treatment with a PD-1/PD-L1 inhibitor; and (iv) treating the patient with the PD-1/PD-L1 inhibitor.

2. The method of claim 1, wherein the PD-1/PD-L1 inhibitor is a PD-L1 inhibitor.

3. The method of claim 1, wherein the PD-1/PD-L1 inhibitor is atezolizumab.

4. The method of claim 1, wherein the cancer is non-small cell lung cancer.

5. The method of claim 1, wherein the patient's tumor cells do not express a detectable level of PD-L1.

6. The method of claim 1, wherein assaying the mRNA expression level of each of XCR1, CXCL9, CXCL10, and CXCL11 comprises nucleotide sequencing.

7. The method of claim 6, wherein determining that the patient's cancer is likely to be responsive to treatment with the PD-1/PD-L1 inhibitor comprises determining that an AP/T score is equal to or greater than a threshold value, wherein the AP/T score is calculated as:

$$AP/T\ \text{score}=\{R(\text{XCR1})+R(\text{CXCL9})+R(\text{CXCL10})+R(\text{CXCL11})\}/4,$$

wherein R for each target mRNA is calculated as follows:

$$R=\log(\text{FPKM value for the target mRNA})-\log(\text{FPKM value for a housekeeping gene}),$$

and wherein "FPKM" is fragments per kilobase of exon per million mapped fragments.

8. The method of claim 1, wherein the method does not include assaying expression level of PD-L1.

* * * * *

SEQUENCE LISTING

<160> NUMBER OF SEQ ID NOS: 16

<210> SEQ ID NO 1
<211> LENGTH: 873
<212> TYPE: DNA
<213> ORGANISM: Homo sapiens

<400> SEQUENCE: 1
atgaggatat ttgctgtctt tatattcatg acctactggc atttgctgaa cgcatttact 60
gtcacggttc ccaaggacct atatgtggta gagtatggta gcaatatgac aattgaatgc 120
aaattcccag tagaaaaaca attagacctg gctgcactaa ttgtctattg ggaaatggag 180
gataagaaca ttattcaatt tgtgcatgga gaggaagacc tgaaggttca gcatagtagc 240
tacagacaga gggcccggct gttgaaggac cagctctccc tgggaaatgc tgcacttcag 300
atcacagatg tgaaattgca ggatgcaggg gtgtaccgct gcatgatcag ctatggtggt 360
gccgactaca agcgaattac tgtgaaagtc aatgccccat acaacaaaat caaccaaaga 420
attttggttg tggatccagt cacctctgaa catgaactga catgtcaggc tgagggctac 480
cccaaggccg aagtcatctg gacaagcagt gaccatcaag tcctgagtgg taagaccacc 540
accaccaatt ccaagagaga ggagaagctt ttcaatgtga ccagcacact gagaatcaac 600
acaacaacta atgagatttt ctactgcact tttaggagat tagatcctga ggaaaaccat 660
acagctgaat tggtcatccc agaactacct ctggcacatc ctccaaatga aaggactcac 720
ttggtaattc tgggagccat cttattatgc cttggtgtag cactgacatt catcttccgt 780
ttaagaaaag ggagaatgat ggatgtgaaa aaatgtggca tccaagatac aaactcaaag 840
aagcaaagtg atacacattt ggaggagacg taa 873

<210> SEQ ID NO 2
<211> LENGTH: 378
<212> TYPE: DNA
<213> ORGANISM: Homo sapiens

<400> SEQUENCE: 2
atgaagaaaa gtggtgttct tttcctcttg ggcatcatct tgctggttct gattggagtg 60
caaggaaccc cagtagtgag aaagggtcgc tgttcctgca tcagcaccaa ccaagggact 120
atccacctac aatccttgaa agaccttaaa caatttgccc caagcccttc ctgcgagaaa 180
attgaaatca ttgctacact gaagaatgga gttcaaacat gtctaaaccc agattcagca 240
gatgtgaagg aactgattaa aaagtgggag aaacaggtca gccaaaagaa aaagcaaaag 300
aatgggaaaa aacatcaaaa aaagaaagtt ctgaaagttc gaaaatctca acgttctcgt 360
caaaagaaga ctacataa 378

<210> SEQ ID NO 3
<211> LENGTH: 297
<212> TYPE: DNA
<213> ORGANISM: Homo sapiens

<400> SEQUENCE: 3
atgaatcaaa ctgccattct gatttgctgc cttatctttc tgactctaag tggcattcaa 60
ggagtacctc tctctagaac tgtacgctgt acctgcatca gcattagtaa tcaacctgtt 120
aatccaaggt ctttagaaaa acttgaaatt attcctgcaa gccaattttg tccacgtgtt 180
gagatcattg ctacaatgaa aaagaagggt gagaagagat gtctgaatcc agaatcgaag 240
gccatcaaga atttactgaa agcagttagc aaggaaaggt ctaaaagatc tccttaa 297

<210> SEQ ID NO 4
<211> LENGTH: 321
<212> TYPE: DNA
<213> ORGANISM: Homo sapiens

<400> SEQUENCE: 4
atgagtgtga agggcatggc tatagccttg gctgtgatat tgtgtgctac agttgttcaa 60
ggcttcccca tgttcaaaag aggacgctgt ctttgcatag gccctggggt aaaagcagtg 120
aaagtggcag atattgagaa agcctccata atgtacccaa gtaacaactg tgacaaaata 180
gaagtgatta ttaccctgaa agaaaataaa ggacaacgat gcctaaatcc caaatcgaag 240
caagcaaggc ttataatcaa attgaaagaa agaattttta aaaatatcaa aacatatgaa 300
gtcctggaaa agagcatctg a 321

<210> SEQ ID NO 5
<211> LENGTH: 1002
<212> TYPE: DNA
<213> ORGANISM: Homo sapiens

<400> SEQUENCE: 5
atggagtcct caggcaaccc agagagcacc acctttttt actatgacct tcagagccag 60
ccgtgtgaga accaggcctg ggtctttgct accctcgcca ccactgtcct atactgcctg 120
gtgtttctcc tcagcctagt gggcaacagc ctggtcctgt gggtcctggt gaagtatgag 180
agcctggagt ccctcaccaa catcttcatc ctcaacctgt gcctctcaga cctggtgttc 240
gcctgcttgt tgcctgtgtg gatctcccca taccactggg gctgggtgct gggagacttc 300
ctctgcaaac tcctcaatat gatcttctcc atcagcctct acagcagcat cttcttcctg 360
accatcatga ccatccaccg ctacctgtcg gtagtgagcc ccctctccac cctgcgcgtc 420
cccaccctcc gctgccgggt gctggtgacc atggctgtgt gggtagccag catcctgtcc 480
tccatcctcg acaccatctt ccacaaggtg ctttcttcgg gctgtgatta ttccgaactc 540
acgtggtacc tcacctccgt ctaccagcac aacctcttct tcctgctgtc cctggggatt 600
atcctgttct gctacgtgga gatcctcagg accctgttcc gctcacgctc caagcggcgc 660
caccgcacgg tcaagctcat cttcgccatc gtggtggcct acttcctcag ctggggtccc 720
tacaacttca ccctgtttct gcagacgctg tttcggaccc agatcatccg gagctgcgag 780
gccaaacagc agctagaata cgccctgctc atctgccgca acctcgcctt ctcccactgc 840
tgctttaacc cggtgctcta tgtcttcgtg ggggtcaagt tccgcacaca cctgaaacat 900
gttctccggc agttctggtt ctgccggctg caggcaccca gcccagcctc gatcccccac 960
tcccctggtg ccttcgccta tgagggcgcc tccttctact ga 1002

<210> SEQ ID NO 6
<211> LENGTH: 726
<212> TYPE: DNA
<213> ORGANISM: Homo sapiens

<400> SEQUENCE: 6
atgcacgagg aagaaatata cacctctctt cagtgggata gcccagcacc agacacttac 60
cagaaatgtc tgtcttccaa caaatgttca ggagcatgct gtcttgtgat ggtgatttca 120
tgtgttttct gcatgggatt attaacagca tccattttct tgggcgtcaa gttgttgcag 180
gtgtccacca ttgcgatgca gcagcaagaa aaactcatcc aacaagagag ggcactgcta 240

```
aactttacag aatggaagag aagctgtgcc cttcagatga aatattgcca agccttcatg    300

caaaactcat taagttcagc ccataacagc agtccttgtc caaacaattg gattcagaac    360

agagaaagtt gttactatgt ctctgaaatt tggagcattt ggcacaccag tcaagagaat    420

tgtttaaagg aaggttccac gctgctacaa atagagagca aagaagaaat ggattttatc    480

actggcagct tgaggaagat taaaggaagc tatgattact gggtggggtt gtctcaggat    540

ggacacagcg gacgctggct ttggcaagat ggctcctctc cttctcctgg cctgttgcca    600

gcagagagat cccagtcagc taaccaagtc tgtggatacg tgaaaagcaa ttcccttctt    660

tcgtctaact gcagcacgtg gaagtatttt atctgtgaga agtatgcgtt gagatcctct    720

gtctga                                                               726


<210> SEQ ID NO 7
<211> LENGTH: 1281
<212> TYPE: DNA
<213> ORGANISM: Homo sapiens

<400> SEQUENCE: 7

atgtgtgacc ggaatggtgg tcggcggctt cgacagtggc tgatcgagca gattgacagt     60

agcatgtatc caggactgat ttgggagaat gaggagaaga gcatgttccg gatcccttgg    120

aaacacgctg gcaagcaaga ttataatcag gaagtggatg cctccatttt taaggcctgg    180

gcagttttta aagggaagtt taaagaaggg gacaaagctg aaccagccac ttggaagacg    240

aggttacgct gtgctttgaa taagagccca gattttgagg aagtgacgga ccggtcccaa    300

ctggacattt ccgagccata caaagtttac cgaattgttc ctgaggaaga gcaaaaatgc    360

aaactaggcg tggcaactgc tggctgcgtg aatgaagtta cagagatgga gtgcggtcgc    420

tctgaaatcg acgagctgat caaggagcct tctgtggacg attacatggg gatgatcaaa    480

aggagccctt ccccgccgga ggcctgtcgg agtcagctcc ttccagactg gtgggcgcag    540

cagcccagca caggcgtgcc gctggtgacg ggtacacca cctacgacgc gcaccattca    600

gcattctccc agatggtgat cagcttctac tatgggggca agctggtggg ccaggccacc    660

accacctgcc ccgagggctg ccgcctgtcc ctgagccagc ctgggctgcc cggcaccaag    720

ctgtatgggc ccgagggcct ggagctggtg cgcttcccgc cggccgacgc catccccagc    780

gagcgacaga ggcaggtgac gcggaagctg ttcgggcacc tggagcgcgg ggtgctgctg    840

cacagcagcc ggcagggcgt gttcgtcaag cggctgtgcc agggccgcgt gttctgcagc    900

ggcaacgccg tggtgtgcaa aggcaggccc aacaagctgg agcgtgatga ggtggtccag    960

gtcttcgaca ccagccagtt cttccgagag ctgcagcagt tctataacag ccagggccgg   1020

cttcctgacg gcagggtggt gctgtgcttt ggggaagagt ttccggatat ggcccccttg   1080

cgctccaaac tcattctcgt gcagattgag cagctgtatg tccggcaact ggcagaagag   1140

gctgggaaga gctgtggagc cggctctgtg atgcaggccc ccgaggagcc gccgccagac   1200

caggtcttcc ggatgtttcc agatatttgt gcctcacacc agagatcatt tttcagagaa   1260

aaccaacaga tcaccgtcta a                                             1281


<210> SEQ ID NO 8
<211> LENGTH: 384
<212> TYPE: DNA
<213> ORGANISM: Homo sapiens

<400> SEQUENCE: 8

atgtcgcaag ggctcccggc cgccggcagc gtcctgcaga ggagcgtcgc ggcgcccggg     60
```

```
aaccagccgc agccgcagcc gcagcagcag agccctgagg atgatgacag gaaggtccga    120

aggagagaaa aaaaccgagt tgctgctcag agaagtcgga agaagcagac ccagaaggct    180

gacaagctcc atgaggaata tgagagcctg gagcaagaaa acaccatgct gcggagagag    240

atcgggaagc tgacagagga gctgaagcac ctgacagagg cactgaagga gcacgagaag    300

atgtgcccgc tgctgctctg ccctatgaac tttgtgccag tgcctccccg gccggaccct    360

gtggccggct gcttgccccg atga                                           384
```

```
<210> SEQ ID NO 9
<211> LENGTH: 290
<212> TYPE: PRT
<213> ORGANISM: Homo sapiens

<400> SEQUENCE: 9

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
            260                 265                 270

Gly Ile Gln Asp Thr Asn Ser Lys Lys Gln Ser Asp Thr His Leu Glu
        275                 280                 285

Glu Thr
    290
```

<210> SEQ ID NO 10
<211> LENGTH: 125
<212> TYPE: PRT
<213> ORGANISM: Homo sapiens

<400> SEQUENCE: 10

```
Met Lys Lys Ser Gly Val Leu Phe Leu Leu Gly Ile Ile Leu Leu Val
1               5                   10                  15

Leu Ile Gly Val Gln Gly Thr Pro Val Val Arg Lys Gly Arg Cys Ser
            20                  25                  30

Cys Ile Ser Thr Asn Gln Gly Thr Ile His Leu Gln Ser Leu Lys Asp
        35                  40                  45

Leu Lys Gln Phe Ala Pro Ser Pro Ser Cys Glu Lys Ile Glu Ile Ile
    50                  55                  60

Ala Thr Leu Lys Asn Gly Val Gln Thr Cys Leu Asn Pro Asp Ser Ala
65                  70                  75                  80

Asp Val Lys Glu Leu Ile Lys Lys Trp Glu Lys Gln Val Ser Gln Lys
                85                  90                  95

Lys Lys Gln Lys Asn Gly Lys Lys His Gln Lys Lys Lys Val Leu Lys
            100                 105                 110

Val Arg Lys Ser Gln Arg Ser Arg Gln Lys Lys Thr Thr
        115                 120                 125
```

<210> SEQ ID NO 11
<211> LENGTH: 98
<212> TYPE: PRT
<213> ORGANISM: Homo sapiens

<400> SEQUENCE: 11

```
Met Asn Gln Thr Ala Ile Leu Ile Cys Cys Leu Ile Phe Leu Thr Leu
1               5                   10                  15

Ser Gly Ile Gln Gly Val Pro Leu Ser Arg Thr Val Arg Cys Thr Cys
            20                  25                  30

Ile Ser Ile Ser Asn Gln Pro Val Asn Pro Arg Ser Leu Glu Lys Leu
        35                  40                  45

Glu Ile Ile Pro Ala Ser Gln Phe Cys Pro Arg Val Glu Ile Ile Ala
    50                  55                  60

Thr Met Lys Lys Lys Gly Glu Lys Arg Cys Leu Asn Pro Glu Ser Lys
65                  70                  75                  80

Ala Ile Lys Asn Leu Leu Lys Ala Val Ser Lys Glu Arg Ser Lys Arg
                85                  90                  95

Ser Pro
```

<210> SEQ ID NO 12
<211> LENGTH: 106
<212> TYPE: PRT
<213> ORGANISM: Homo sapiens

<400> SEQUENCE: 12

```
Met Ser Val Lys Gly Met Ala Ile Ala Leu Ala Val Ile Leu Cys Ala
1               5                   10                  15

Thr Val Val Gln Gly Phe Pro Met Phe Lys Arg Gly Arg Cys Leu Cys
            20                  25                  30

Ile Gly Pro Gly Val Lys Ala Val Lys Val Ala Asp Ile Glu Lys Ala
        35                  40                  45

Ser Ile Met Tyr Pro Ser Asn Asn Cys Asp Lys Ile Glu Val Ile Ile
    50                  55                  60
```

-continued

Thr Leu Lys Glu Asn Lys Gly Gln Arg Cys Leu Asn Pro Lys Ser Lys
65 70 75 80

Gln Ala Arg Leu Ile Ile Lys Leu Lys Glu Arg Ile Phe Lys Asn Ile
85 90 95

Lys Thr Tyr Glu Val Leu Glu Lys Ser Ile
100 105

<210> SEQ ID NO 13
<211> LENGTH: 333
<212> TYPE: PRT
<213> ORGANISM: Homo sapiens

<400> SEQUENCE: 13

Met Glu Ser Ser Gly Asn Pro Glu Ser Thr Thr Phe Phe Tyr Tyr Asp
1 5 10 15

Leu Gln Ser Gln Pro Cys Glu Asn Gln Ala Trp Val Phe Ala Thr Leu
20 25 30

Ala Thr Thr Val Leu Tyr Cys Leu Val Phe Leu Leu Ser Leu Val Gly
35 40 45

Asn Ser Leu Val Leu Trp Val Leu Val Lys Tyr Glu Ser Leu Glu Ser
50 55 60

Leu Thr Asn Ile Phe Ile Leu Asn Leu Cys Leu Ser Asp Leu Val Phe
65 70 75 80

Ala Cys Leu Leu Pro Val Trp Ile Ser Pro Tyr His Trp Gly Trp Val
85 90 95

Leu Gly Asp Phe Leu Cys Lys Leu Leu Asn Met Ile Phe Ser Ile Ser
100 105 110

Leu Tyr Ser Ser Ile Phe Phe Leu Thr Ile Met Thr Ile His Arg Tyr
115 120 125

Leu Ser Val Val Ser Pro Leu Ser Thr Leu Arg Val Pro Thr Leu Arg
130 135 140

Cys Arg Val Leu Val Thr Met Ala Val Trp Val Ala Ser Ile Leu Ser
145 150 155 160

Ser Ile Leu Asp Thr Ile Phe His Lys Val Leu Ser Ser Gly Cys Asp
165 170 175

Tyr Ser Glu Leu Thr Trp Tyr Leu Thr Ser Val Tyr Gln His Asn Leu
180 185 190

Phe Phe Leu Leu Ser Leu Gly Ile Ile Leu Phe Cys Tyr Val Glu Ile
195 200 205

Leu Arg Thr Leu Phe Arg Ser Arg Ser Lys Arg Arg His Arg Thr Val
210 215 220

Lys Leu Ile Phe Ala Ile Val Val Ala Tyr Phe Leu Ser Trp Gly Pro
225 230 235 240

Tyr Asn Phe Thr Leu Phe Leu Gln Thr Leu Phe Arg Thr Gln Ile Ile
245 250 255

Arg Ser Cys Glu Ala Lys Gln Gln Leu Glu Tyr Ala Leu Leu Ile Cys
260 265 270

Arg Asn Leu Ala Phe Ser His Cys Cys Phe Asn Pro Val Leu Tyr Val
275 280 285

Phe Val Gly Val Lys Phe Arg Thr His Leu Lys His Val Leu Arg Gln
290 295 300

Phe Trp Phe Cys Arg Leu Gln Ala Pro Ser Pro Ala Ser Ile Pro His
305 310 315 320

Ser Pro Gly Ala Phe Ala Tyr Glu Gly Ala Ser Phe Tyr
325 330

<210> SEQ ID NO 14
<211> LENGTH: 241
<212> TYPE: PRT
<213> ORGANISM: Homo sapiens

<400> SEQUENCE: 14

Met His Glu Glu Glu Ile Tyr Thr Ser Leu Gln Trp Asp Ser Pro Ala
1 5 10 15

Pro Asp Thr Tyr Gln Lys Cys Leu Ser Ser Asn Lys Cys Ser Gly Ala
20 25 30

Cys Cys Leu Val Met Val Ile Ser Cys Val Phe Cys Met Gly Leu Leu
35 40 45

Thr Ala Ser Ile Phe Leu Gly Val Lys Leu Leu Gln Val Ser Thr Ile
50 55 60

Ala Met Gln Gln Gln Glu Lys Leu Ile Gln Gln Glu Arg Ala Leu Leu
65 70 75 80

Asn Phe Thr Glu Trp Lys Arg Ser Cys Ala Leu Gln Met Lys Tyr Cys
85 90 95

Gln Ala Phe Met Gln Asn Ser Leu Ser Ser Ala His Asn Ser Ser Pro
100 105 110

Cys Pro Asn Asn Trp Ile Gln Asn Arg Glu Ser Cys Tyr Tyr Val Ser
115 120 125

Glu Ile Trp Ser Ile Trp His Thr Ser Gln Glu Asn Cys Leu Lys Glu
130 135 140

Gly Ser Thr Leu Leu Gln Ile Glu Ser Lys Glu Glu Met Asp Phe Ile
145 150 155 160

Thr Gly Ser Leu Arg Lys Ile Lys Gly Ser Tyr Asp Tyr Trp Val Gly
165 170 175

Leu Ser Gln Asp Gly His Ser Gly Arg Trp Leu Trp Gln Asp Gly Ser
180 185 190

Ser Pro Ser Pro Gly Leu Leu Pro Ala Glu Arg Ser Gln Ser Ala Asn
195 200 205

Gln Val Cys Gly Tyr Val Lys Ser Asn Ser Leu Leu Ser Ser Asn Cys
210 215 220

Ser Thr Trp Lys Tyr Phe Ile Cys Glu Lys Tyr Ala Leu Arg Ser Ser
225 230 235 240

Val

<210> SEQ ID NO 15
<211> LENGTH: 426
<212> TYPE: PRT
<213> ORGANISM: Homo sapiens

<400> SEQUENCE: 15

Met Cys Asp Arg Asn Gly Gly Arg Arg Leu Arg Gln Trp Leu Ile Glu
1 5 10 15

Gln Ile Asp Ser Ser Met Tyr Pro Gly Leu Ile Trp Glu Asn Glu Glu
20 25 30

Lys Ser Met Phe Arg Ile Pro Trp Lys His Ala Gly Lys Gln Asp Tyr
35 40 45

Asn Gln Glu Val Asp Ala Ser Ile Phe Lys Ala Trp Ala Val Phe Lys
50 55 60

Gly Lys Phe Lys Glu Gly Asp Lys Ala Glu Pro Ala Thr Trp Lys Thr
65 70 75 80

```
Arg Leu Arg Cys Ala Leu Asn Lys Ser Pro Asp Phe Glu Glu Val Thr
                85                  90                  95

Asp Arg Ser Gln Leu Asp Ile Ser Glu Pro Tyr Lys Val Tyr Arg Ile
            100                 105                 110

Val Pro Glu Glu Glu Gln Lys Cys Lys Leu Gly Val Ala Thr Ala Gly
        115                 120                 125

Cys Val Asn Glu Val Thr Glu Met Glu Cys Gly Arg Ser Glu Ile Asp
    130                 135                 140

Glu Leu Ile Lys Glu Pro Ser Val Asp Asp Tyr Met Gly Met Ile Lys
145                 150                 155                 160

Arg Ser Pro Ser Pro Pro Glu Ala Cys Arg Ser Gln Leu Leu Pro Asp
                165                 170                 175

Trp Trp Ala Gln Gln Pro Ser Thr Gly Val Pro Leu Val Thr Gly Tyr
            180                 185                 190

Thr Thr Tyr Asp Ala His His Ser Ala Phe Ser Gln Met Val Ile Ser
        195                 200                 205

Phe Tyr Tyr Gly Gly Lys Leu Val Gly Gln Ala Thr Thr Thr Cys Pro
    210                 215                 220

Glu Gly Cys Arg Leu Ser Leu Ser Gln Pro Gly Leu Pro Gly Thr Lys
225                 230                 235                 240

Leu Tyr Gly Pro Glu Gly Leu Glu Leu Val Arg Phe Pro Pro Ala Asp
                245                 250                 255

Ala Ile Pro Ser Glu Arg Gln Arg Gln Val Thr Arg Lys Leu Phe Gly
            260                 265                 270

His Leu Glu Arg Gly Val Leu Leu His Ser Ser Arg Gln Gly Val Phe
        275                 280                 285

Val Lys Arg Leu Cys Gln Gly Arg Val Phe Cys Ser Gly Asn Ala Val
    290                 295                 300

Val Cys Lys Gly Arg Pro Asn Lys Leu Glu Arg Asp Glu Val Val Gln
305                 310                 315                 320

Val Phe Asp Thr Ser Gln Phe Phe Arg Glu Leu Gln Gln Phe Tyr Asn
                325                 330                 335

Ser Gln Gly Arg Leu Pro Asp Gly Arg Val Val Leu Cys Phe Gly Glu
            340                 345                 350

Glu Phe Pro Asp Met Ala Pro Leu Arg Ser Lys Leu Ile Leu Val Gln
        355                 360                 365

Ile Glu Gln Leu Tyr Val Arg Gln Leu Ala Glu Glu Ala Gly Lys Ser
    370                 375                 380

Cys Gly Ala Gly Ser Val Met Gln Ala Pro Glu Glu Pro Pro Pro Asp
385                 390                 395                 400

Gln Val Phe Arg Met Phe Pro Asp Ile Cys Ala Ser His Gln Arg Ser
                405                 410                 415

Phe Phe Arg Glu Asn Gln Gln Ile Thr Val
            420                 425
```

<210> SEQ ID NO 16
<211> LENGTH: 127
<212> TYPE: PRT
<213> ORGANISM: Homo sapiens

<400> SEQUENCE: 16

```
Met Ser Gln Gly Leu Pro Ala Ala Gly Ser Val Leu Gln Arg Ser Val
1               5                   10                  15

Ala Ala Pro Gly Asn Gln Pro Gln Pro Gln Pro Gln Gln Gln Ser Pro
            20                  25                  30
```

-continued

```
Glu Asp Asp Asp Arg Lys Val Arg Arg Arg Glu Lys Asn Arg Val Ala
        35                  40                  45

Ala Gln Arg Ser Arg Lys Lys Gln Thr Gln Lys Ala Asp Lys Leu His
    50                  55                  60

Glu Glu Tyr Glu Ser Leu Glu Gln Glu Asn Thr Met Leu Arg Arg Glu
65                  70                  75                  80

Ile Gly Lys Leu Thr Glu Glu Leu Lys His Leu Thr Glu Ala Leu Lys
                85                  90                  95

Glu His Glu Lys Met Cys Pro Leu Leu Leu Cys Pro Met Asn Phe Val
            100                 105                 110

Pro Val Pro Pro Arg Pro Asp Pro Val Ala Gly Cys Leu Pro Arg
        115                 120                 125
```